US006884789B2

(12) United States Patent
Davis et al.

(10) Patent No.: US 6,884,789 B2
(45) Date of Patent: Apr. 26, 2005

(54) LINEAR CYCLODEXTRIN COPOLYMERS

(75) Inventors: Mark E. Davis, Pasadena, CA (US); Hector Gonzalez, San Francisco, CA (US); Suzie (Sue Jean) Hwang, Torrance, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/097,326

(22) Filed: Mar. 15, 2002

(65) Prior Publication Data

US 2002/0151523 A1 Oct. 17, 2002

Related U.S. Application Data

(60) Division of application No. 09/339,818, filed on Jun. 25, 1999, which is a continuation-in-part of application No. 09/203,556, filed on Dec. 2, 1998, now Pat. No. 6,509,323.
(60) Provisional application No. 60/091,550, filed on Jul. 1, 1998.

(51) Int. Cl.$^7$ ...................... A61K 31/715; C08B 37/16; C08B 31/18
(52) U.S. Cl. .......................... 514/58; 536/103; 536/105; 536/106; 536/124
(58) Field of Search ................................ 536/103, 105; 536/106, 124; 514/58

(56) References Cited

U.S. PATENT DOCUMENTS

| | | | | |
|---|---|---|---|---|
| RE32,268 E | * | 10/1986 | Gordon ........................ | 514/25 |
| 4,727,064 A | | 2/1988 | Pitha ............................ | 514/58 |
| 4,774,329 A | | 9/1988 | Friedman ..................... | 536/103 |
| 4,902,788 A | | 2/1990 | Zemel et al. ................. | 536/1.1 |
| 4,941,996 A | | 7/1990 | Trend et al. ................. | 252/584 |
| 5,275,824 A | | 1/1994 | Carli et al. .................. | 424/490 |
| 5,276,088 A | * | 1/1994 | Yoshinaga .................. | 525/54.3 |
| 5,357,012 A | | 10/1994 | Nussstein et al. ......... | 526/238.2 |
| 5,488,102 A | | 1/1996 | Vetter .......................... | 536/32 |
| 5,547,932 A | | 8/1996 | Curiel et al. ................. | 435/65 |
| 5,571,882 A | | 11/1996 | Vetter ....................... | 526/238.2 |
| 5,608,015 A | * | 3/1997 | Yoshinaga ................... | 526/75 |
| 5,612,389 A | | 3/1997 | Chabrecek et al. ........... | 522/35 |
| 5,635,383 A | | 6/1997 | Wu et al. ................. | 435/172.3 |
| 5,691,316 A | | 11/1997 | Agrawal et al. .............. | 514/44 |
| 5,693,768 A | | 12/1997 | Bachmann et al. .......... | 536/4.1 |
| 6,009,155 A | * | 12/1999 | Davis et al. .................. | 514/58 |
| 6,048,736 A | * | 4/2000 | Kosak ......................... | 436/536 |
| 6,132,734 A | * | 10/2000 | Thomas et al. .......... | 424/275.1 |
| 2001/0034333 A1 | | 10/2001 | Krosak ........................ | 514/44 |
| 2001/0044412 A1 | | 11/2001 | Wolff et al. .................... | 514/44 |

FOREIGN PATENT DOCUMENTS

| | | |
|---|---|---|
| EP | 0 502 194 A | 9/1992 |
| EP | 0 587 106 A2 | 3/1994 |
| FR | 2 665 169 | 1/1992 |
| JP | 3-221505 | 9/1991 |
| JP | 9-263535 | 10/1997 |
| WO | WO 93/05084 | 3/1993 |
| WO | WO 96/09073 A1 | 3/1996 |
| WO | WO 97/33044 | 9/1997 |
| WO | WO 00/01734 A1 * | 1/2000 |
| WO | WO 00/33885 A1 * | 6/2000 |
| WO | WO 00/40962 | 7/2000 |
| WO | WO 00/75162 | 12/2000 |
| WO | WO 00/75164 | 12/2000 |
| WO | WO 01/37665 | 5/2001 |

OTHER PUBLICATIONS

Pierce 1989 Handbook and General Catalog, Rockford, Illinois, 1989, only pp. 288–293 supplied, month of publication data is unavailable.*
Tabushi et al., "Artficial Receptor Recognizing Hydrophobic Carbonyl Compounds," *Journal of Organic Chemistry*, 51(10), 1918–1921 (Mar. 16, 1986).*
Boussif et al., "A Versatile Vector for Gene and Oligonucleotide Transfer into Cells in Culture and in Vivo: Polyethylenimine," Natl. Acad. Sci. USA, 92:7297–7301, Aug. 1995.
Crini et al., "Linear Cyclodextrin–poly(Vinylamine); Synthesis and NMR Characterization," Eur. Polym. J., 33(7): 1143–1151, Jul. 1997.
Cserháti et al., "Charge–Transfer Chromatographi Study of the Complex Formation of Some Anticancer Drugs with γ–Cyclodextrin," Analytical Biochemistry, 225:328–332, 1995.
Database WPI, Week 199221, JP 410–6101, "Cyclodextrin Polymer with Asymmetry Discriminating Ability—Prepd. By Copolymerising Cyclodextrin with Bifunctional Carbonyl Cpd., used as Filler for Gas Chromatography" Apr. 8, 1992 (Abstract Only).
Deratani et al., "Linear cyclodextrin–containing polyelectrolytes 1. Synthesis of poly(1–vinylimidazole)–supported β–cyclodextrin. Effect of pH and ionic strength on the solution behaviour," Macromol. Chem. Phys., 196:343–352, 1995.
Fieser et al., Reagents for Organic Synthesis, vol. 3, pp. 265–266, Wiley, New York, 1967.
Gao et al., "Potentiation of Cationic Liposome–Mediated Gene Delivery by Polycations," Biochemistry, 35:1027–1036, 1996.
Habus et al., "Synthesis, Hybridization Properties, Nuclease Stability, and Cellular Uptake of the Oligonucleotide–Amino–β–cyclodextrins and Adamantance Conjugates," Bioconjugate Chem., 6(4):327–331, Jul./Aug. 1995.

(Continued)

Primary Examiner—L. E. Crane
(74) Attorney, Agent, or Firm—Ropes & Gray, LLP

(57) ABSTRACT

Linear cyclodextrin copolymers and linear oxidized cyclodextrin copolymers containing an unoxidized and/or an oxidized cyclodextrin moiety integrated into the polymer backbone are described. Methods of preparing such copolymers are also described. The linear cyclodextrin copolymer and linear oxidized cyclodextrin copolymer of the invention may be used as a delivery vehicle of various therapeutic agents.

19 Claims, 5 Drawing Sheets

OTHER PUBLICATIONS

Hisamatsu et al., "Study on Specific Modification of Glucosyl Cyclodextrins," Starch, 44: 188–191, 1992.

Husain et al., "Complexation of Doxorubicin with β– and γ–Cyclodextrins," Applied Spectroscopy, 46(4):652–658, 1992.

Jicsinszky et al., "Comprehensive Supramolecular Chemistry," vol. 3, Chap. 4, pp. 138–185, Szejtli et al., Eds., Pergamon, 1996.

Karunaratne et al., "Synthesis of Bulky β–Lactams for Inhibition of Cell Surface β–Lactamase Acitivity," Bioconjugate Chem., 4:434–439, 1993.

Liu et al., "Sugar–containing Polyamines Prepared Using Galactose Oxidase Coupled with Chemical Reduction," J. Am. Chem. Soc., 121:466–467, 1999 (published on web Dec. 29, 1998).

Lowry et al., "Protein Measurement with the Folin Phenol Reagent," J. Biol, Chem., 193:265–275, 1951.

Mungall et al., "Use of the Azido Group in the Synthesis of 5'Terminal Aminodeoxythymidine Oligonucleotides," J. Org. Chem., 40(11):1659–1662, 1975.

Tabushi et al., "Characterization of Regiospecific A,C– and A, D–Disulfonate Capping of β–Cyclodextrin. Capping as an Efficient Production Technique," J. Am. Chem. Soc., 106, 5267–5270, 1984.

Tabushi et al., "Bis(histamino)cyclodextrin–Zn–Imidazole Complex as an Artificial Carbonic Anhydrase," J. Am. Chem. Soc., 106, 4580–4584, 1984.

Tabushi et al., "Specific Bifuntionalization on Cyclodextrin," Tetrahedron Lett., 18:1527–1530, 1977.

Tanaka et al., "Synthesis of Doxorubicin–cyclodextrin Conjugates," J. Antibiotics, 47(9): 1025–1029, Sep. 1994.

Uekama et al., "Cyclodextrin Drug Carrier Systems," Chem. Rev., 98:2045–2076, 1998 (published on web Jun. 6, 1998).

Zanta et al., "In Vitro Gene Delivery to Hepatocytes with Galatosylated Polyethylenimine," Bioconjugate Chemistry, 8:839–844, 1997.

* cited by examiner

LINEAR CYCLODEXTRIN COPOLYMERS

CROSS REFERENCE TO RELATED APPLICATIONS

This is a divisional patent application filed under 35 U.S.C. § 121 of the copending U.S. application Ser. No. 09/339,818, filed Jun. 25, 1999, which is a continuation-in-part application claiming benefit of priority under 35 U.S.C. § 120 to U.S. application Ser. No. 09/203,556, filed Dec. 2, 1998, now U.S. Pat. No. 6,509,323 which claims benefit under 35 U.S.C. § 119(e) to U.S. Provisional Application Ser. No. 60/091,550, filed Jul. 1, 1998, each of which is herein incorporated by reference in its entirety.

BACKGROUND OF THE INVENTION

1. Field of the Invention

The invention relates to linear cyclodextrin copolymers and linear oxidized cyclodextrin copolymers. These copolymers, respectively, contain a cyclodextrin moiety, unoxidized or oxidized, as a monomer unit integrated into the copolymer backbone. The invention also relates methods of preparing linear cyclodextrin copolymers and linear oxidized cyclodextrin copolymers. Such cyclodextrin copolymers may be used as a delivery vehicle of various therapeutic agents.

2. Background of the Invention

Cyclodextrins are cyclic polysaccharides containing naturally occurring D(+)-glucopyranose units in an α-(1,4) linkage. The most common cyclodextrins are alpha (α)-cyclodextrins, beta (β)-cyclodextrins and gamma (γ)-cyclodextrins which contain, respectively. six, seven or eight glucopyranose units. Structurally, the cyclic nature of a cyclodextrin forms a torus or donut-like shape having an inner apolar or hydrophobic cavity, the secondary hydroxyl groups situated on one side of the cyclodextrin torus and the primary hydroxyl groups situated on the other. Thus, using (β)-cyclodextrin as an example, a cyclodextrin is often represented schematically as follows:

The side on which the secondary hydroxyl groups are located has a wider diameter than the side on which the primary hydroxyl groups are located. The hydrophobic nature of the cyclodextrin inner cavity allows for the inclusion of a variety of compounds. (*Comprehensive Supramolecular Chemistry*, Volume 3, J. L. Atwood et al., eds., Pergamon Press (1996); T. Cserhati, *Analytical Biochemistry*, 225:328–332 (1995); Husain et al., *Applied Spectroscopy*, 46:652–658 (1992); FR 2 665 169).

Cyclodextrins have been used as a delivery vehicle of various therapeutic compounds by forming inclusion complexes with various drugs that can fit into the hydrophobic cavity of the cyclodextrin or by forming non-covalent association complexes with other biologically active molecules such as oligonucleotides and derivatives thereof. For example, U.S. Pat. No. 4,727,064 describes pharmaceutical preparations consisting of a drug with substantially low water solubility and an amorphous, water-soluble cyclodextrin-based mixture. The drug forms an inclusion complex with the Cyclodextrins of the mixture. In U.S. Pat. No. 5,691,316, a cyclodextrin cellular delivery system for oligonucleotides is described. In such a system, an oligonucleotide is noncovalently complexed with a cyclodextrin or, alternatively, the oligonucleotide may be covalently bound to adamantine which in turn is non-covalently associated with a cyclodextrin.

Various cyclodextrin containing polymers and methods of their preparation are also known in the art. (*Comprehensive Supramolecular Chemistry*, Volume 3, J. L. Atwood et al., eds., Pergamon Press (1996)). A process for producing a polymer containing immobilized cyclodextrin is described in U.S. Pat. No. 5,608,015. According to the process, a cyclodextrin derivative is reacted with either an acid halide monomer of an α,β-unsaturated acid or derivative thereof or with an α,γ-unsaturated acid or derivative thereof having a terminal isocyanate group or a derivative thereof. The cyclodextrin derivative is obtained by reacting cyclodextrin with such compounds as carbonyl halides and acid anhydrides. The resulting polymer contains cyclodextrin units as side chains off a linear polymer main chain.

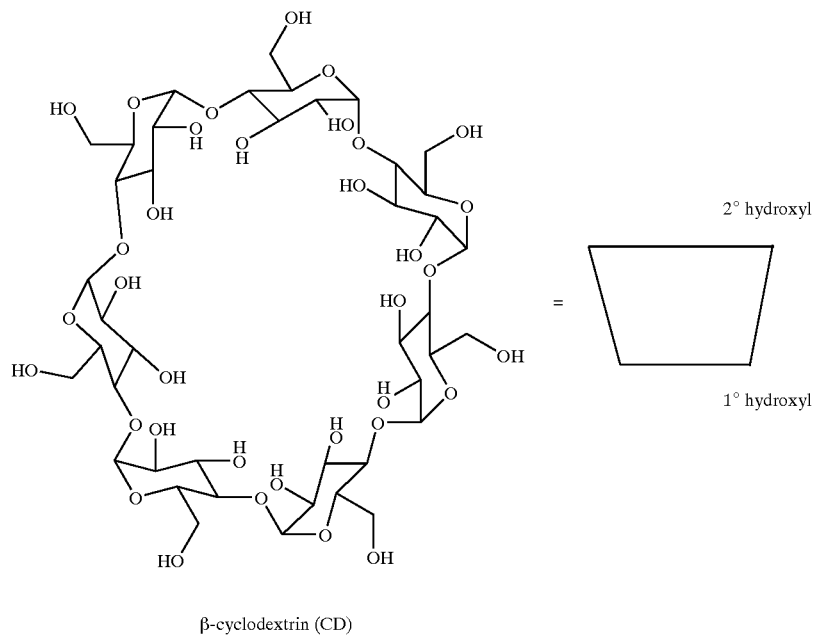

β-cyclodextrin (CD)

U.S. Pat. No. 5,276,088 describes a method of synthesizing cyclodextrin polymers by either reacting polyvinyl alcohol or cellulose or derivatives thereof with cyclodextrin derivatives or by copolymerization of a cyclodextrin derivative with vinyl acetate or methyl methacrylate. Again, the resulting cyclodextrin polymer contains a cyclodextrin moiety as a pendant moiety off the main chain of the polymer.

A biodegradable medicinal polymer assembly with Supramolecular structure is described in WO 96/09073 A1. The assembly comprises a number of drug-carrying cyclic compounds prepared by binding a drug to an α, β, or γ-cyclodextrin and then stringing the drug/cyclodextrin compounds along a linear polymer with the biodegradable moieties bound to both ends of the polymer. Such an assembly is reportably capable of releasing a drug in response to a specific biodegradation occurring in a disease. These assemblies are commonly referred to as "necklace-type" cyclodextrin polymers.

However, there still exists a need in the art for linear cyclodextrin polymers in which the cyclodextrin moiety is part of the main chain and not a pendant moiety off the main chain and a method for their preparation.

SUMMARY OF THE INVENTION

This invention answers this need by providing a linear cyclodextrin copolymer. Such a linear cyclodextrin copolymer has a repeating unit of formula Ia, Ib, or a combination thereof:

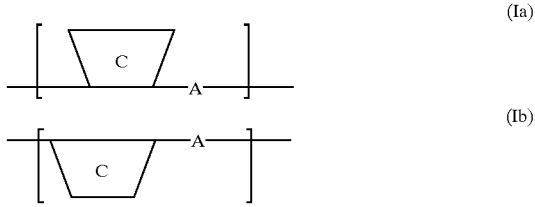

The invention also provides methods of preparing a linear cyclodextrin copolymer. One method copolymerizes a cyclodextrin monomer precursor disubstituted with the same or different leaving group and a comonomer A precursor capable of displacing the leaving group. Another such method involves iodinating a cyclodextrin monomer precursor to form a diiodinated cyclodextrin monomer precursor and then copolymerizing the diiodinated cyclodextrin monomer precursor with a comonomer A precursor to produce the linear cyclodextrin copolymer. Another method involves iodinating a cyclodextrin monomer precursor to form a diiodinated cyclodextrin monomer precursor, aminating the diiodinated cyclodextrin monomer precursor to form a diaminated cyclodextrin monomer precursor and then copolymerizing the diaminated cyclodextrin monomer precursor with a comonomer A precursor to produce the linear cyclodextrin copolymer. Yet another method involves the reduction of a linear oxidized cyclodextrin copolymer to the linear cyclodextrin copolymer.

The invention further provides a linear oxidized cyclodextrin copolymer. A linear oxidized cyclodextrin copolymer is a linear cyclodextrin copolymer which contains at least one oxidized cyclodextrin moiety of formula VIa or VIb:

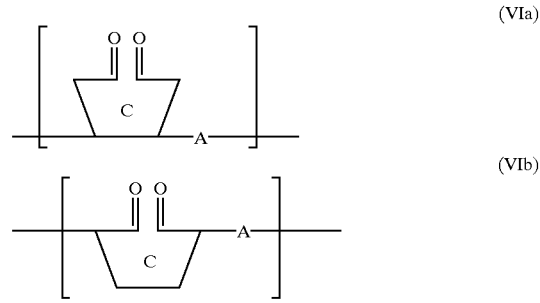

Each cyclodextrin moiety of a linear cyclodextrin copolymer of the invention may be oxidized so as to form a linear oxidized cyclodextrin copolymer having a repeating unit of formula VIa, VIb, or a combination thereof.

The invention also provides a method of preparing a linear oxidized cyclodextrin copolymer. One method involves oxidizing a linear cyclodextrin copolymer such that at least one cyclodextrin monomer is oxidized. Other methods involve copolymerizing an oxidized cyclodextrin monomer precursor with a comonomer A precursor.

The invention still further provides a linear cyclodextrin copolymer or linear oxidized cyclodextrin copolymer grafted onto a substrate and a method of their preparation. The invention also provides a linear cyclodextrin copolymer or linear oxidized cyclodextrin copolymer crosslinked to another polymer and a method of their preparation. A method of preparing crosslinked cyclodextrin polymers involves reacting a linear or linear oxidized cyclodextrin copolymer with a polymer in the presence of a crosslinking agent.

The invention provides a linear cyclodextrin copolymer or linear oxidized cyclodextrin copolymer having at least one ligand bound to the cyclodextrin copolymer. The ligand may be bound to either the cyclodextrin moiety or the comonomer A moiety of the copolymer.

The invention also provides a cyclodextrin composition containing at least one linear cyclodextrin copolymer of the invention and at least one linear oxidized cyclodextrin copolymer of the invention. The invention also provides therapeutic compositions containing a therapeutic agent and a linear cyclodextrin copolymer and/or a linear oxidized cyclodextrin copolymer of the invention. A method of treatment by administering a therapeutically effective amount of a therapeutic composition of the invention is also described.

DETAILED DESCRIPTION OF THE INVENTION

Figure 1A:
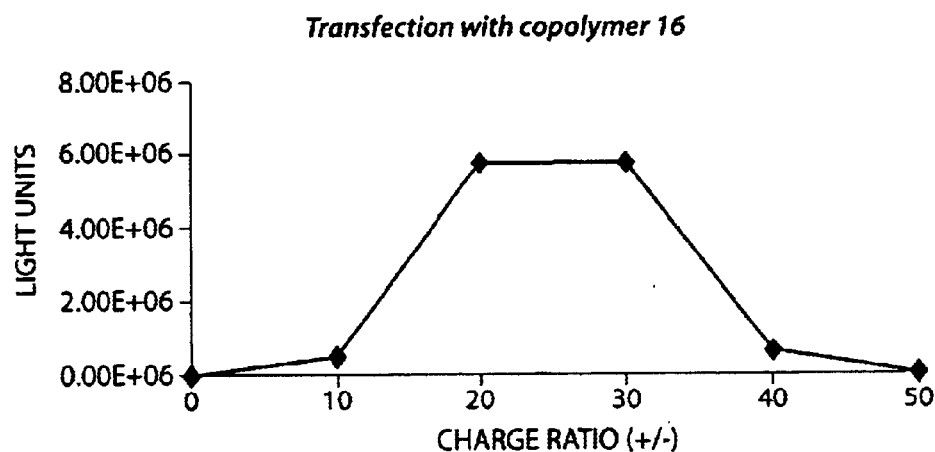
FIG. 1A shows transfection studies with plasmids encoding *Luciferase* reporter gene particularly noting the transfection with copolymer 16.

One embodiment of the invention is a linear cyclodextrin copolymer. A linear cyclodextrin copolymer is a polymer containing cyclodextrin moieties as an integral part of its polymer backbone. Previously, cyclodextrin moieties were not a part of the main polymer chain but rather attached off a polymer backbone as pendant moieties.

According to the invention, a linear cyclodextrin copolymer has a repeating unit of formula Ia, Ib, or a combination thereof:

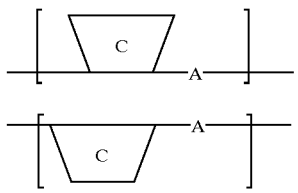

In formula Ia and Ib, C is a substituted or unsubstituted cyclodextrin monomer and A is a comonomer bound, i.e. covalently bound, to cyclodextrin C. Polymerization of a cyclodextrin monomer C precursor with a comonomer A precursor results in a linear cyclodextrin copolymer of the invention. Within a single linear cyclodextrin copolymer of the invention, the cyclodextrin monomer C unit may be the same or different and, likewise, the comonomer A may be the same or different.

A cyclodextrin monomer precursor may be any cyclodextrin or derivative thereof known in the art. As discussed above, a cyclodextrin is defined as a cyclic polysaccharide most commonly containing six to eight naturally occurring D(+)-glucopyranose units in an α-(1,4) linkage. Preferably, the cyclodextrin monomer precursor is a cyclodextrin having six, seven and eight glucose units, i.e., respectively, an alpha (α)-cyclodextrin, a beta (β)-cyclodextrin and a gamma (γ)-cyclodextrin. A cyclodextrin derivative may be any substituted cyclodextrin known in the art where the substituent does not interfere with copolymerization with comonomer A precursor as described below. According to the invention, a cyclodextrin derivative may be neutral, cationic or anionic. Examples of suitable substituents include, but are not limited to, hydroxyalkyl groups, such as, for example, hydroxypropyl, hydroxyethyl; ether groups, such as, for example, dihydroxypropyl ethers, methyl-hydroxyethyl ethers, ethyl-hydroxyethyl ethers, and ethyl-hydroxypropyl ethers; alkyl groups, such as, for example, methyl; saccharides, such as, for example, glucosyl and maltosyl; acid groups, such as, for example, carboxylic acids, phosphorous acids, phosphinous acids, phosphonic acids, phosphoric acids, thiophosphonic acids, thiophosphonic acid and sulfonic acids; imidazole groups; and sulfate groups.

A cyclodextrin monomer precursor may be further chemically modified (e.g. halogenated, aminated) to facilitate or affect copolymerization of the cyclodextrin monomer precursor with a comonomer A precursor, as described below. Chemical modification of a cyclodextrin monomer precursor allows for polymerization at only two positions on each cyclodextrin moiety, i.e. the creation of a bifunctional cyclodextrin moiety. The numbering scheme for the C1–C6 positions of each glucopyranose ring is as follows:

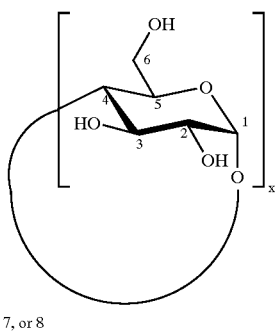

X = 6, 7, or 8

In a preferred embodiment, polymerization occurs at two of any C2, C3 and C6 position, including combinations thereof, of the cyclodextrin moiety. For example, one cyclodextrin monomer precursor may be polymerized at two C6 positions while another cyclodextrin monomer precursor may be polymerized at a C2 and a C6 position of the cyclodextrin moiety. Using β-cyclodextrin as an example, the lettering scheme for the relative position of each glucopyranose ring in a cyclodextrin is as follows:

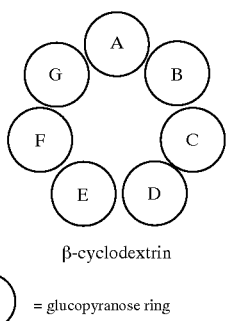

β-cyclodextrin

◯ = glucopyranose ring

In a preferred embodiment of a linear cyclodextrin copolymer of the invention, the cyclodextrin monomer C has the following general formula (II):

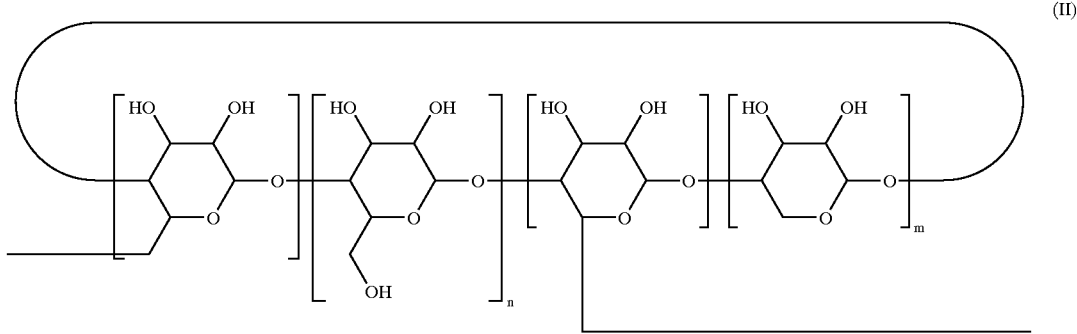

(II)

In formula (II), n and m represent integers which, along with the other two glucopyranose rings, define the total number of glucopyranose units in the cyclodextrin monomer. Formula (II) represents a cyclodextrin monomer which is capable of being polymerized at two C6 positions on the cyclodextrin unit. Examples of cyclodextrin monomers of formula (II) include, but are not limited to, $6^A,6^B$-deoxy-α-cyclodextrin (n=0, m=4), $6^A,6^C$-deoxy-α-cyclodextrin (n=1, m=3), $6^A,6^D$-deoxy-α-cyclodextrin (n=2, m=2), $6^A,6^B$-deoxy-β-cyclodextrin (n=0, m=5), $6^A,6^C$-deoxy-β-cyclodextrin (n=1, m=4), $6^A,6^D$-deoxy-β-cyclodextrin (n=2, m=3), $6^A,6^B$-deoxy-γ-cyclodextrin (n=0, m=6), $6^A,6^C$-deoxy-γ-cyclodextrin (n=1, m=5), $6^A,6^D$-deoxy-γ-cyclodextrin (n=2, m=4), and $6^A,6^E$-deoxy-γ-cyclodextrin (n=3, m=3). In another preferred embodiment of linear cyclodextrin copolymer of the invention, a cyclodextrin monomer C unit has the following general formula (III):

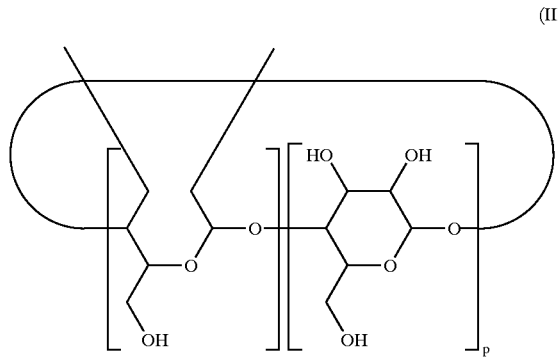

(III)

where p=5–7. In formula (III), one of D(+)-glucopyranose units of a cyclodextrin monomer has undergone ring opening to allow for polymerization at a C2 and a C3 position of the cyclodextrin unit. Cyclodextrin monomers of formula (III) are commercially available from Carbomer of Westborough, Mass. Examples of cyclodextrin monomers of formula (III) include, but are not limited to, $2^A,3^A$-deoxy-$2^A,3^A$-dihydro-α-cyclodextrin, $2^A,3^A$-deoxy-$2^A,3^A$-dihydro-β-cyclodextrin, $2^A,3^A$-deoxy-$2^A,3^A$-dihydro-γ-cyclodextrin, commonly referred to as, respectively, 2,3-deoxy-α-cyclodextrin, 2,3-deoxy-β-cyclodextrin, and 2,3-deoxy-γ-cyclodextrin.

A comonomer A precursor may be any straight chain or branched, symmetric or asymmetric compound which upon reaction with a cyclodextrin monomer precursor, as described above, links two cyclodextrin monomers together. Preferably, a comonomer A precursor is a compound containing at least two functional groups through which reaction and thus linkage of the cyclodextrin monomers can be achieved. Examples of possible functional groups, which may be the same or different, terminal or internal, of each comonomer A precursor include, but are not limited to, amino, acid, ester, imidazole, and acyl halide groups and derivatives thereof. In a preferred embodiment, the two functional groups are the same and terminal. Upon copolymerization of a comonomer A precursor with a cyclodextrin monomer precursor, two cyclodextrin monomers may be linked together by joining the primary hydroxyl side of one cyclodextrin monomer with the primary hydroxyl side of another cyclodextrin monomer, by joining the secondary hydroxyl side of one cyclodextrin monomer with the secondary hydroxyl side of another cyclodextrin monomer, or by joining the primary hydroxyl side of one cyclodextrin monomer with the secondary hydroxyl side of another cyclodextrin monomer. Accordingly, combinations of such linkages may exist in the final copolymer. Both the comonomer A precursor and the comonomer A of the final copolymer may be neutral, cationic (e.g. by containing protonated groups such as, for example, quaternary ammonium groups) or anionic (e.g. by containing deprotonated groups, such as, for example, sulfate, phosphate or carboxylate anionic groups). The charge of comonomer A of the copolymer may be adjusted by adjusting pH conditions. Examples of suitable comonomer A precursors include, but are not limited to, cystamine, 1,6-diaminohexane, diimidazole, dithioimidazole, spermine, dithiospermine, dihistidine, dithiohistidine, succinimide (e.g. dithiobis(succinimidyl propionate) (DSP) and disuccinimidyl suberate (DSS)) and imidates (e.g. dimethyl 3,3'-dithiobispropionimidate (DTBP)). Copolymerization of a comonomer A precursor with a cyclodextrin monomer precursor leads to the formation of a linear cyclodextrin copolymer of the invention containing comonomer A linkages of the following general formulae:

—HNC(O)($CH_2$)$_x$C(O)NH—, —HNC(O)($CH_2$)$_x$SS($CH_2$)$_x$C(O)NH—, —$^+H_2$N($CH_2$)$_x$SS($CH_2$)$_x$$NH_2^+$—, —HNC(O)($CH_2CH_2O$)$_x$$CH_2CH_2$C(O)NH—, —HNNHC(O)($CH_2CH_2O$)$_x$$CH_2CH_2$C(O)NHNH—, —$^+H_2$N$CH_2$($CH_2CH_2O$)$_x$$CH_2CH_2CH_2$$NH_2^+$—, —HNC(O)($CH_2CH_2O$)$_x$$CH_2CH_2$SS($CH_2CH_2O$)$_x$$CH_2CH_2$C(O)NH—, —HNC($NH_2^+$)($CH_2CH_2O$)$_x$$CH_2CH_2$C($NH_2^+$)NH—, —S$CH_2CH_2$NHC($NH_2^+$)($CH_2$)$_x$C($NH_2^+$)NH$CH_2CH_2$S—, —S$CH_2CH_2$NHC($NH_2^+$)($CH_2$)$_x$SS($CH_2$)$_x$C($NH_2^+$)NH$CH_2CH_2$S—, —S$CH_2CH_2$NHC($NH_2^+$)$CH_2CH_2$(O$CH_2CH_2$)$_x$C (NH$_2^+$)NHCH$_2$CH$_2$S—,

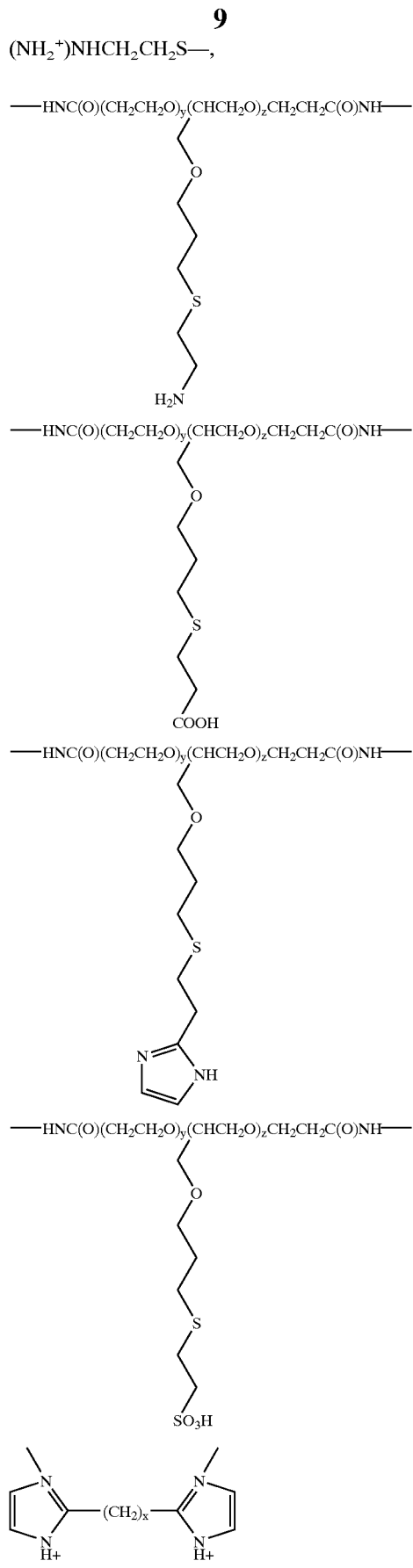

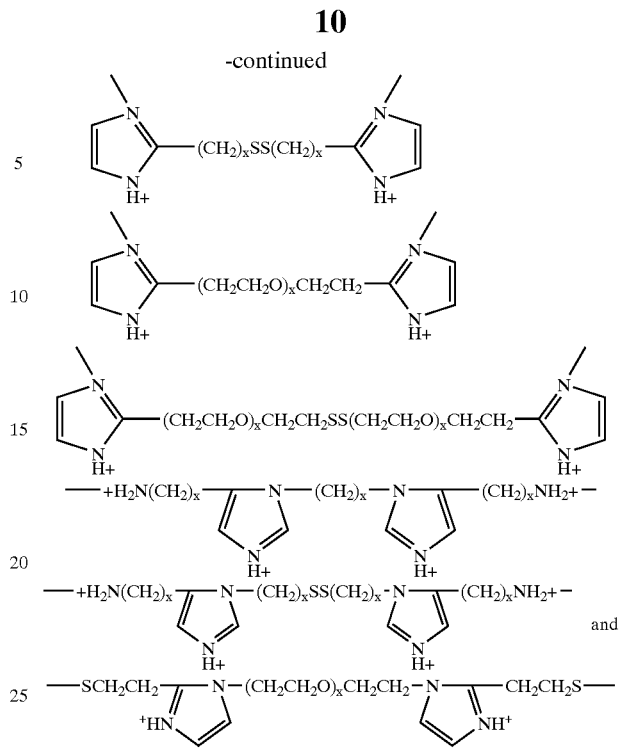

In the above formulae, x=1–50, and y+z=x. Preferably, x=1–30. More preferably, x=1–20. In a preferred embodiment, comonomer A is biodegradable or acid-labile. Also in a preferred embodiment, the comonomer A precursor and hence the comonomer A may be selectively chosen in order to achieve a desired application. For example, to deliver small molecular therapeutic agents, a charged polymer may not be necessary and the comonomer A may be a polyethylene glycol group.

A linear cyclodextrin copolymer of the invention may be modified with at least one ligand attached to the cyclodextrin copolymer. The ligand may be attached to the cyclodextrin copolymer through the cyclodextrin monomer C or comonomer A. Preferably, the ligand is attached to at least one cyclodextrin moiety of the linear cyclodextrin copolymer. Preferably, the ligand allows a linear cyclodextrin copolymer to target and bind to a cell. If more than one ligand, which may be the same or different, is attached to a linear cyclodextrin copolymer of the invention, the additional ligand or ligands may be bound to the same or different cyclodextrin moiety or the same or different comonomer A of the copolymer. Examples of suitable ligands include, but are not limited to, vitamins (e.g. folic acid), proteins (e.g. transferrin, and monoclonal antibodies) and polysaccharides. The ligand will vary depending upon the type of delivery desired. For example, receptor-mediated delivery may by achieved by, but not limited to, the use of a folic acid ligand while antisense oligo delivery may be achieved by, but not limited to, use of a transferrin ligand. The ligand may be attached to a copolymer of the invention by means known in the art.

Another embodiment of the invention is a method of preparing a linear cyclodextrin copolymer. According to the invention, a linear cyclodextrin copolymer of the invention may be prepared by copolymerizing a cyclodextrin monomer precursor disubstituted with an appropriate leaving group with a comonomer A precursor capable of displacing the leaving groups. The leaving group, which may be the same or different, may be any leaving group known in the art which may be displaced upon copolymerization with a comonomer A precursor. In a preferred embodiment, a linear cyclodextrin copolymer may be prepared by iodinating a cyclodextrin monomer precursor to form a diiodinated cyclodextrin monomer precursor and copolymerizing the diiodinated cyclodextrin monomer precursor with a comonomer A precursor to form a linear cyclodextrin copolymer having a repeating unit of formula Ia, Ib, or a combination thereof, each as described above. In a preferred embodiment, a method of preparing a linear cyclodextrin of the invention iodinates a cyclodextrin monomer precursor as described above to form a diiodinated cyclodextrin monomer precursor of formula IVa, IVb, IVc or a mixture thereof:

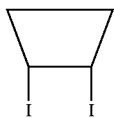

(IVa)

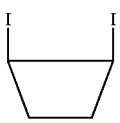

(IVb)

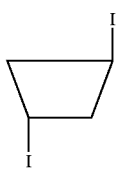

(IVc)

The diiodinated cyclodextrin may be prepared by any means known in the art. (Tabushi et al. *J. Am. Chem.* 106, 5267–5270 (1984); Tabushi et al. *J. Am. Chem.* 106, 4580–4584 (1984)). For example, β-cyclodextrin may be reacted with biphenyl-4,4'-disulfonyl chloride in the presence of anhydrous pyridine to form a biphenyl-4,4'-disulfonyl chloride capped β-cyclodextrin which may then be reacted with potassium iodide to produce diiodo-β-cyclodextrin. The cyclodextrin monomer precursor is iodinated at only two positions. By copolymerizing the diiodinated cyclodextrin monomer precursor with a comonomer A precursor, as described above, a linear cyclodextrin polymer having a repeating unit of formula Ia, Ib, or a combination thereof, also as described above, may be prepared. If appropriate, the iodine or iodo groups may be replaced with other known leaving groups.

Also according to the invention, the iodo groups or other appropriate leaving group may be displaced with a group that permits reaction with a comonomer A precursor, as described above. For example, a diiodinated cyclodextrin monomer precursor of formula IVa, IVb, IVc or a mixture thereof may be aminated to form a diaminated cyclodextrin monomer precursor of formula Va, Vb, Vc or a mixture thereof:

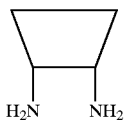

(Va)

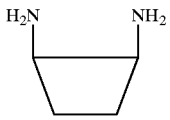

(Vb)

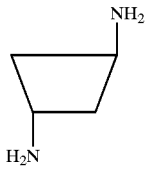

(Vc)

The diaminated cyclodextrin monomer precursor may be prepared by any means known in the art. (Tabushi et al. *Tetrahedron Lett.* 18:1527–1530 (1977); Mungall et al., *J. Org. Chem.* 1659–1662 (1975)). For example, a diiodo-β-cyclodextrin may be reacted with sodium azide and then reduced to form a diamino-β-cyclodextrin. The cyclodextrin monomer precursor is aminated at only two positions. The diaminated cyclodextrin monomer precursor may then be copolymerized with a comonomer A precursor, as described above, to produce a linear cyclodextrin copolymer having a repeating unit of formula Ia, Ib, or a combination thereof, also as described above. However, the amino functionality of a diaminated cyclodextrin monomer precursor need not be directly attached to the cyclodextrin moiety. Alternatively, the amino functionality may be introduced by displacement of the iodo or other appropriate leaving groups of a cyclodextrin monomer precursor with amino group containing moieties such as, for example, —SCH$_2$CH$_2$NH$_2$, to form a diaminated cyclodextrin monomer precursor of formula Vd, Ve, Vf or a mixture thereof:

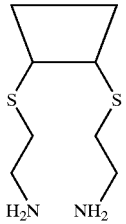

(Vd)

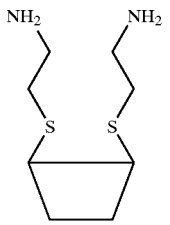

(Ve)

(Vf)

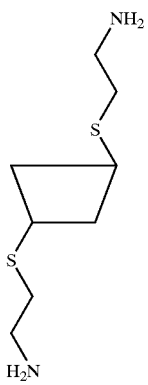

A linear cyclodextrin copolymer of the invention may also be prepared by reducing a linear oxidized cyclodextrin copolymer of the invention as described below. This method may be performed as long as the comonomer A does not contain a reducible moiety or group such as, for example, a disulfide linkage.

According to the invention, a linear cyclodextrin copolymer of the invention may be oxidized so as to introduce at least one oxidized cyclodextrin monomer into the copolymer such that the oxidized cyclodextrin monomer is an integral part of the polymer backbone. A linear cyclodextrin copolymer which contains at least one oxidized cyclodextrin monomer is defined as a linear oxidized cyclodextrin copolymer. The cyclodextrin monomer may be oxidized on either the secondary or primary hydroxyl side of the cyclodextrin moiety. If more than one oxidized cyclodextrin monomer is present in a linear oxidized cyclodextrin copolymer of the invention, the same or different cyclodextrin monomers oxidized on either the primary hydroxyl side, the secondary hydroxyl side, or both may be present. For illustration purposes, a linear oxidized cyclodextrin copolymer with oxidized secondary hydroxyl groups has, for example, at least one unit of formula VIa or VIb:

(VIa)

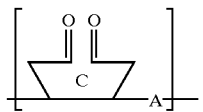

(VIb)

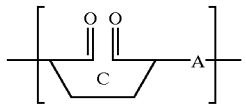

In formulae VIa and VIb, C is a substituted or unsubstituted oxidized cyclodextrin monomer and A is a comonomer bound, i.e. covalently bound, to the oxidized cyclodextrin C. Also in formulae VIa and VIb, oxidation of the secondary hydroxyl groups leads to ring opening of the cyclodextrin moiety and the formation of aldehyde groups.

A linear oxidized cyclodextrin copolymer may be prepared by oxidation of a linear cyclodextrin copolymer as discussed above. Oxidation of a linear cyclodextrin copolymer of the invention may be accomplished by oxidation techniques known in the art. (Hisamatsu et al., *Starch* 44:188–191 (1992)). Preferably, an oxidant such as, for example, sodium periodate is used. It would be understood by one of ordinary skill in the art that under standard oxidation conditions that the degree of oxidation may vary or be varied per copolymer. Thus in one embodiment of the invention, a linear oxidized copolymer of the invention may contain one oxidized cyclodextrin monomer. In another embodiment, substantially all to all cyclodextrin monomers of the copolymer would be oxidized.

Another method of preparing a linear oxidized cyclodextrin copolymer of the invention involves the oxidation of a diiodinated or diaminated cyclodextrin monomer precursor, as described above, to form an oxidized diiodinated or diaminated cyclodextrin monomer precursor and copolymerization of the oxidized diiodinated or diaminated cyclodextrin monomer precursor with a comonomer A precursor. In a preferred embodiment, an oxidized diiodinated cyclodextrin monomer precursor of formula VIIa, VIIb, VIIc, or a mixture thereof:

(VIIa)

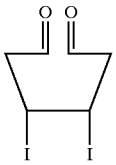

(VIIb)

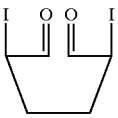

(VIIc)

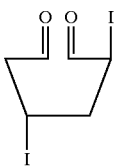

may be prepared by oxidation of a diiodinated cyclodextrin monomer precursor of formulae IVa, IVb, IVc, or a mixture thereof, as described above. In another preferred embodiment, an oxidized diaminated cyclodextrin monomer precursor of formula VIIIa, VIIIb, VIIIc or a mixture thereof:

(VIIIa)

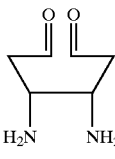

(VIIIb)

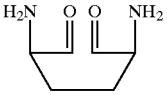

(VIIIc)

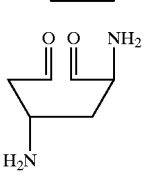

may be prepared by amination of an oxidized diiodinated cyclodextrin monomer precursor of formulae VIIa, VIIb, VIIc, or a mixture thereof, as described above. In still another preferred embodiment, an oxidized diaminated cyclodextrin monomer precursor of formula IXa, IXb, IXc or a mixture thereof:

(IXa)

(IXb)

(IXc)

may be prepared by displacement of the iodo or other appropriate leaving groups of an oxidized cyclodextrin monomer precursor disubstituted with an iodo or other appropriate leaving group with the amino group containing moiety —SCH$_2$CH$_2$NH$_2$.

Alternatively, an oxidized diiodinated or diaminated cyclodextrin monomer precursor, as described above, may be prepared by oxidizing a cyclodextrin monomer precursor to form an oxidized cyclodextrin monomer precursor and then diiodinating and/or diaminating the oxidized cyclodextrin monomer, as described above. As discussed above, the cyclodextrin moiety may be modified with other leaving groups other than iodo groups and other amino group containing functionalities. The oxidized diiodinated or diaminated cyclodextrin monomer precursor may then be copolymerized with a comonomer A precursor, as described above, to form a linear oxidized cyclodextrin copolymer of the invention.

A linear oxidized cyclodextrin copolymer may also be further modified by attachment of at least one ligand to the copolymer. The ligand is as described above.

In a preferred embodiment of the invention, a linear cyclodextrin copolymer or a linear oxidized cyclodextrin copolymer terminates with at least one comonomer A precursor or hydrolyzed product of the comonomer A precursor, each as described above. As a result of termination of the cyclodextrin copolymer with at least one comonomer A precursor, at least one free functional group, as described above, exists per linear cyclodextrin copolymer or per linear oxidized cyclodextrin copolymer. For example, the functional group may be an acid group or a functional group that may be hydrolyzed to an acid group. According to the invention, the functional group may be further chemically modified as desired to enhance the properties of the cyclodextrin copolymer, such as, for example, colloidal stability, and transfection efficiency. For example, the functional group may be modified by reaction with PEG to form a PEG terminated cyclodextrin copolymer to enhance colloidal stability or with histidine to form an imidazolyl terminated cyclodextrin copolymer to enhance intracellular and transfection efficiency.

Further chemistry may be performed on the cyclodextrin copolymer through the modified functional group. For example, the modified functional group may be used to extend a polymer chain by linking a linear cyclodextrin copolymer or linear oxidized cyclodextrin copolymer, as described herein, to the same or different cyclodextrin copolymer or to a non-cyclodextrin polymer. In a preferred embodiment of the invention, the polymer to be added on is the same or different linear cyclodextrin copolymer or linear oxidized cyclodextrin copolymer which may also terminated with at least one comonomer A precursor for further modification, each as described herein.

Alternatively, at least two of the same or different linear cyclodextrin copolymers or linear oxidized cyclodextrin copolymers containing a terminal functional group or a terminal modified functional group, as described above, may be reacted and linked together through the functional or modified functional group. Preferably, upon reaction of the functional or modified functional groups, a degradable moiety such as, for example, a disulfide linkage is formed. For example, modification of the terminal functional group with cysteine may be used to produce a linear cyclodextrin copolymer or linear oxidized cyclodextrin copolymer having at least one free thiol group. Reaction with the same or different cyclodextrin copolymer also containing at least one free thiol group will form a disulfide linkage between the two copolymers. In a preferred embodiment of the invention, the functional or modified functional groups may be selected to offer linkages exhibiting different rates of degradation (e.g. via enzymatic degradation) and thereby provide, if desired, a time release system for a therapeutic agent. The resulting polymer may be crosslinked, as described herein. A therapeutic agent, as described herein, may be added prior to or post crosslinking of the polymer. A ligand, as described herein, may also be bound through the modified functional group.

According to the invention, a linear cyclodextrin copolymer or linear oxidized cyclodextrin copolymer may be attached to or grafted onto a substrate. The substrate may be any substrate as recognized by those of ordinary skill in the art. In another preferred embodiment of the invention, a linear cyclodextrin copolymer or linear oxidized cyclodextrin copolymer may be crosslinked to a polymer to form, respectively, a crosslinked cyclodextrin copolymer or a crosslinked oxidized cyclodextrin copolymer. The polymer may be any polymer capable of crosslinking with a linear or linear oxidized cyclodextrin copolymer of the invention (e.g. polyethylene glycol (PEG) polymer, polyethylene polymer). The polymer may also be the same or different linear cyclodextrin copolymer or linear oxidized cyclodextrin copolymer. Thus, for example, a linear cyclodextrin copolymer may be crosslinked to any polymer including, but not limited to, itself, another linear cyclodextrin copolymer, and a linear oxidized cyclodextrin copolymer. A crosslinked linear cyclodextrin copolymer of the invention may be prepared by reacting a linear cyclodextrin copolymer with a polymer in the presence of a crosslinking agent. A crosslinked linear oxidized cyclodextrin copolymer of the invention may be prepared by reacting a linear oxidized cyclodextrin copolymer with a polymer in the presence of an appropriate crosslinking agent. The crosslinking agent may be any crosslinking agent known in the art. Examples of crosslinking agents include dihydrazides and disulfides. In a preferred embodiment, the crosslinking agent is a labile group such that a crosslinked copolymer may be uncrosslinked if desired.

A linear cyclodextrin copolymer and a linear oxidized cyclodextrin copolymer of the invention may be characterized by any means known in the art. Such characterization methods or techniques include, but are not limited to, gel permeation chromatography (GPC), matrix assisted laser desorption ionization-time of flight mass spectrometry (MALDI-TOF Mass spec), $^1$H and $^{13}$C NMR, light scattering and titration.

The invention also provides a cyclodextrin composition containing at least one linear cyclodextrin copolymer and at least one linear oxidized cyclodextrin copolymer of the invention as described above. Accordingly, either or both of the linear cyclodextrin copolymer and linear oxidized cyclodextrin copolymer may be crosslinked to another polymer and/or bound to a ligand as described above. Therapeutic compositions according to the invention contain a therapeutic agent and a linear cyclodextrin copolymer or a linear oxidized cyclodextrin copolymer, including crosslinked copolymers, of the invention. A linear cyclodextrin copolymer, a linear oxidized cyclodextrin copolymer and their crosslinked derivatives are as described above. The therapeutic agent may be any synthetic or naturally occurring biologically active therapeutic agent including those known in the art. Examples of suitable therapeutic agents include, but are not limited to, antibiotics, steroids, polynucleotides (e.g. genomic DNA, cDNA, mRNA and antisense oligonucleotides), plasmids, peptides, peptide fragments, small molecules (e.g. doxorubicin) and other biologically active macromolecules such as, for example, proteins and enzymes.

A therapeutic composition of the invention may be prepared by means known in the art. In a preferred embodiment, a copolymer of the invention is mixed with a therapeutic agent, as described above, and allowed to self-assemble. According to the invention, the therapeutic agent and a linear cyclodextrin copolymer or a linear oxidized cyclodextrin copolymer of the invention associate with one another such that the copolymer acts as a delivery vehicle for the therapeutic agent. The therapeutic agent and cyclodextrin copolymer may associate by means recognized by those of skill in the art such as, for example, electrostatic interaction and hydrophobic interaction. The degree of association may be determined by techniques known in the art including, for example, fluorescence studies, DNA mobility studies, light scattering, electron microscopy, and will vary depending upon the therapeutic agent. As a mode of delivery, for example, a therapeutic composition of the invention containing a copolymer of the invention and DNA may be used to aid in transfection, i.e. the uptake of DNA into an animal (e.g. human) cell. (Boussif, O. *Proceedings of the National Academy of Sciences*, 92:7297–7301 (1995); Zanta et al. *Bioconjugate Chemistry*, 8:839–844 (1997)).

A therapeutic composition of the invention may be, for example, a solid, liquid, suspension, or emulsion. Preferably a therapeutic composition of the invention is in a form that can be injected intravenously. Other modes of administration of a therapeutic composition of the invention include, depending on the state of the therapeutic composition, methods known in the art such as, but not limited to, oral administration, topical application, parenteral, intravenous, intranasal, intraocular, intracranial or intraperitoneal injection.

Depending upon the type of therapeutic agent used, a therapeutic composition of the invention may be used in a variety of therapeutic methods (e.g. DNA vaccines, antibiotics, antiviral agents) for the treatment of inherited or acquired disorders such as, for example, cystic fibrosis, Gaucher's disease, muscular dystrophy, AIDS, cancers (e.g. multiple myeloma, leukemia, melanoma, and ovarian carcinoma), cardiovascular conditions (e.g., progressive heart failure, restenosis, and hemophilia), and neurological conditions (e.g. brain trauma). According to the invention, a method of treatment administers a therapeutically effective amount of a therapeutic composition of the invention. A therapeutically effective amount, as recognized by those of skill in the art, will be determined on a case by case basis. Factors to be considered include, but are not limited to, the disorder to be treated and the physical characteristics of the one suffering from the disorder.

Another embodiment of the invention is a composition containing at least one biologically active compound having agricultural utility and a linear cyclodextrin copolymer or a linear oxidized cyclodextrin copolymer of the invention. The agriculturally biologically active compounds include those known in the art. For example, suitable agriculturally biologically active compounds include, but are not limited to, fungicides, herbicides, insecticides, and mildewcides.

The following examples are given to illustrate the invention. It should be understood, however, that the invention is not to be limited to the specific conditions or details described in these examples.

EXAMPLES

Materials. β-cyclodextrin (Cerestar USA, Inc. of Hammond, Ind.) was dried in vacuo (<0.1 mTorr) at 120° C. for 12 h before use. Biphenyl-4,4'-disulfonyl chloride (Aldrich Chemical Company, Inc. of Milwaukee, Wis.) was recrystallized from chloroform/hexanes. Potassium iodide was powdered with a mortar and pestle and dried in an oven at 200° C. All other reagents were obtained from commercial suppliers and were used as received without further purification. Polymer samples were analyzed on a Hitachi HPLC system equipped with an Anspec RI detector and a Progel-TSK G3000$_{PWXL}$ column using water as eluant at a 1.0 mL min$^{-1}$ flow rate.

Example 1

Biphenyl-4,4'-disulfonyl-A,D-Capped β-Cyclodextrin, 1 (Tabushi et al. *J. Am. Chem. Soc.* 106, 5267–5270 (1984))

A 500 mL round bottom flask equipped with a magnetic stirbar, a Schlenk adapter and a septum was charged with 7.92 g (6.98 mmol) of dry β-cyclodextrin and 250 mL of anhydrous pyridine (Aldrich Chemical Company, Inc.). The resulting solution was stirred at 50° C. under nitrogen while 2.204 g (6.28 mmol) of biphenyl-4,4'-disulfonyl chloride was added in four equal portions at 15 min intervals. After stirring at 50 ° C. for an additional 3 h, the solvent was removed in vacuo and the residue was subjected to reversed-phase column chromatography using a gradient elution of 0–40% acetonitrile in water. Fractions were analyzed by high performance liquid chromatography (HPLC) and the appropriate fractions were combined. After removing the bulk of the acetonitrile on a rotary evaporator, the resulting aqueous suspension was lyophilized to dryness. This afforded 3.39 g (38%) of 1 as a colorless solid.

Example 2

$6^A,6^D$-Diiodo-$6^A,6^D$-Deoxy-β-cyclodextrin, 2 (Tabushi et al. *J. Am. Chem.* 106, 4580–4584 (1984))

A 40 mL centrifuge tube equipped with a magnetic stirbar, a Schlenk adapter and a septum was charged with 1.02 g (7.2 mmol) of 1, 3.54 g (21.3 mmol) of dry, powdered potassium iodide (Aldrich) and 15 mL of anhydrous N,N-dimethylformamide (DMF) (Aldrich). The resulting suspension was stirred at 80° C. under nitrogen for 2 h. After cooling to room temperature, the solids were separated by centrifugation and the supernatant was decanted. The solid precipitate was washed with a second portion of anhydrous DMF and the supernatants were combined and concentrated in vacuo. The residue was then dissolved in 14 mL of water and cooled in an ice bath before 0.75 mL (7.3 mmol) of tetrachloroethylene (Aldrich) was added with rapid stirring. The precipitated inclusion complex was filtered on a medium glass frit and washed with a small portion of acetone before it was dried under vacuum over $P_2O_5$ for 14 h. This afforded 0.90 g (92%) of 2 as a white solid.

Example 3

$6^A,6^D$-Diazido-$6^A,6^D$-Deoxy-β-cyclodextrin, 3 (Tabushi et al. *Tetrahedron Lett.* 18, 1527–1530 (1977))

A 100 mL round bottom flask equipped with a magnetic stirbar, a Schlenk adapter and a septum was charged with 1.704 g (1.25 mmol) of β-cyclodextrin diiodide, 0.49 g (7.53 mmol) of sodium azide (EM Science of Gibbstown, N.J.) and 10 mL of anhydrous N,N-dimethylformamide (DMF). The resulting suspension was stirred at 60° C. under nitrogen for 14 h. The solvent was then removed in vacuo. The resulting residue was dissolved in enough water to make a 0.2 M solution in salt and then passed through 11.3 g of Biorad AG501-X8(D) resin to remove residual salts. The eluant was then lyophilized to dryness yielding 1.232 g (83%) of 3 as a white amorphous solid which was carried on to the next step without further purification.

Example 4

$6^A,6^D$-Diamino-$6^A,6^D$-Deoxy-β-cyclodextrin, 4 (Mungall et al., *J. Org. Chem.* 1659–1662 (1975))

A 250 mL round bottom flask equipped with a magnetic stirbar and a septum was charged with 1.232 g (1.04 mmol) of β-cyclodextrin bisazide and 50 mL of anhydrous pyridine (Aldrich). To this stirring suspension was added 0.898 g (3.42 mmol) of triphenylphosphine. The resulting suspension was stirred for 1 h at ambient temperature before 10 mL of concentrated aqueous ammonia was added. The addition of ammonia was accompanied by a rapid gas evolution and the solution became homogeneous. After 14 h, the solvent was removed in vacuo and the residue was triterated with 50 mL of water. The solids were filtered off and the filtrate was made acidic (pH<4) with 10% HCl before it was applied to an ion exchange column containing Toyopearl SP-650M ($NH_4^+$form) resin. The product 4 was eluted with a gradient of 0–0.5 M ammonium bicarbonate. Appropriate fractions were combined and lyophilized to yield 0.832 g (71%) of the product 4 as the bis(hydrogen carbonate) salt.

Example 5

β-cyclodextrin-DSP copolymer, 5

A 20 mL scintillation vial was charged with a solution of 92.6 mg ($7.65 \times 10^{-5}$ mol) of the bis(hydrogen carbonate) salt of 4 in 1 mL of water. The pH of the solution was adjusted to 10 with 1 M NaOH before a solution of 30.9 mg ($7.65 \times 10^{-5}$ mol) of dithiobis(succinimidyl propionate) (DSP, Pierce Chemical Co. of Rockford, Ill.) in 1 mL of chloroform was added. The resulting biphasic mixture was agitated with a Vortex mixer for 0.5 h. The aqueous layer was then decanted and extracted with 3×1 mL of fresh chloroform. The aqueous polymer solution was then subjected to gel permeation chromatography (GPC) on Toyopearl HW-40F resin using water as eluant. Fractions were analyzed by GPC and appropriate fractions were lyophilized to yield 85 mg (85%) as a colorless amorphous powder.

Example 6

β-cyclodextrin-DSS copolymer, 6

A β-cyclodextrin-DSS copolymer, 6, was synthesized in a manner analogous to the DSP polymer, 5, except that disuccinimidyl suberate (DSS, Pierce Chemical Co. of Rockford, Ill.) was substituted for the DSP reagent. Compound 6 was obtained in 67% yield.

Example 7

β-cyclodextrin-DTBP copolymer, 7

A 20 mL scintillation vial was charged with a solution of 91.2 mg ($7.26 \times 10^{-5}$ mol) of the bis(hydrogen carbonate) salt of 4 in 1 mL of water. The pH of the solution was adjusted to 10 with 1 M NaOH before 22.4 mg ($7.26 \times 10^{-5}$ mol) of dimethyl 3,3'-dithiobis(propionimidate).2 HCl (DTBP, Pierce Chemical Co. of Rockford, Ill.) was added. The resulting homogeneous solution was agitated with a Vortex mixer for 0.5 h. The aqueous polymer solution was then subjected to gel permeation chromatography (GPC) on Toyopearl HW-40F resin. Fractions were analyzed by GPC and appropriate fractions were lyophilized to yield 67 mg (67%) of a colorless amorphous powder.

Example 8

β-cyclodextrin-cystamine copolymer, 8

To a solution of 166.2 mg ($7.38 \times 10^{-5}$ mol) of cystamine dihydrochloride (Aldrich) in 15 mL of 0.1 N NaOH was added 100 mg ($7.38 \times 10^{-5}$ mol) of 2 and 5 mL of acetonitrile. The resulting homogeneous solution was heated at 80° C. for 2 h before it was subjected to gel permeation chromatography (GPC) on Toyopearl HW-40F resin. Fractions were analyzed by GPC and appropriate fractions were lyophilized to yield 17.2 mg (19%) of a colorless amorphous powder.

Example 9

Polyethylene glycol 600 dihydrazide, 9

A 100 mL round bottom flask equipped with a magnetic stirbar and a reflux condenser was charged with 1.82 g (3.0 mmol) of polyethylene glycol 600 (Fluka Chemical Corp of Milwaukee, Wis.), 40 mL of absolute ethanol (Quantum Chemicals Pty Ltd of Tuscola, Ill.) and a few drops of sulfuric acid. The resulting solution was heated to reflux for 14 h. Solid sodium carbonate was added to quench the reaction and the solution of the PEG diester was transferred under nitrogen to an addition funnel. This solution was then added dropwise to a solution of 0.6 mL (9.0 mmol) of hydrazine hydrate (Aldrich) in 10 mL of absolute ethanol. A small amount of a cloudy precipitate formed. The resulting solution was heated to reflux for 1 h before it was filtered and concentrated. GPC analysis revealed a higher molecular weight impurity contaminating the product. Gel permeation chromatography on Toyopearl HW-40 resin enabled a partial purification of this material to approximately 85% purity.

Example 10

Oxidation of β-cyclodextrin-DSS copolymer, 10 (Hisamatsu et al., *Starch* 44, 188–191 (1992))

The β-cyclodextrin-DSS copolymer 6 (92.8 mg, 7.3×10$^{-5}$ mol) was dissolved in 1.0 mL of water and cooled in an ice bath before 14.8 mg (7.3×10$^{-5}$ mol) of sodium periodate was added. The solution immediately turned bright yellow and was allowed to stir in the dark at 0° C. for 14 h. The solution was then subjected to gel permeation chromatography (GPC) on Toyopearl HW-40 resin using water as eluant. Fractions were analyzed by GPC. Appropriate fractions were combined and lyophilized to dryness to yield 84.2 mg (91%) of a light brown amorphous solid.

Example 11

Polyethylene glycol (PEG) 600 diacid chloride, 11

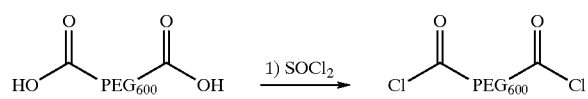

A 50 mL round bottom flask equipped with a magnetic stirbar and a reflux condenser was charged with 5.07 g (ca. 8.4 mmol) of polyethylene glycol 600 diacid (Fluka Chemical Corp of Milwaukee, Wis.) and 10 mL of anhydrous chloroform (Aldrich). To this stirring solution was added 3.9 mL (53.4 mmol) of thionyl chloride (Aldrich) and the resulting solution was heated to reflux for 1 h, during which time gas evolution was evident. The resulting solution was allowed to cool to room temperature before the solvent and excess thionyl chloride were removed in vacuo. The resulting oil was stored in a dry box and used without purification.

Example 12

β-cyclodextrin-PEG 600 copolymer, 12

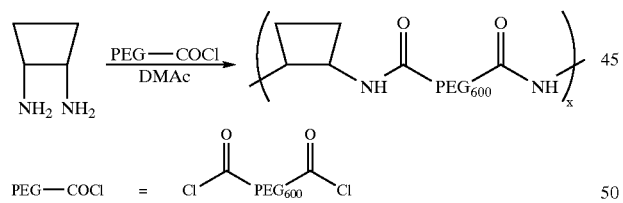

A 20 mL scintillation vial was charged with a solution of 112.5 mg (8.95×10$^{-5}$ mol) of the bis(hydrogen carbonate) salt of 6$^A$,6$^D$-diamino-6$^A$,6$^D$-deoxy-β-cyclodextrin, 50 μL (3.6×10$^{-4}$ mol) of triethylamine (Aldrich), and 5 mL of anhydrous N,N-dimethylacetamide (DMAc, Aldrich). The resulting suspension was then treated with 58 mg (9.1×10$^{-5}$ mol) of polyethylene glycol 600 diacid chloride, 11. The resulting solution was agitated with a Vortex mixer for 5 minutes and then allowed to stand at 25° C. for 1 h during which time it became homogeneous. The solvent was removed in vacuo and the residue was subjected to gel permeation chromatography on Toyopearl HW-40F resin using water as eluant. Fractions were analyzed by GPC and appropriate fractions were lyophilized to dryness to yield 115 mg (75%) of a colorless amorphous powder.

Example 13

β-cyclodextrin-DSP copolymer, 13

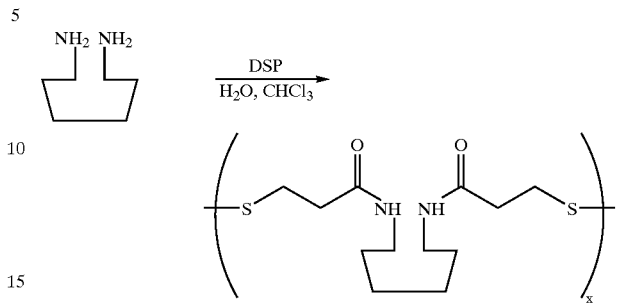

A 8 mL vial was charged with a solution of 102.3 mg (8.80×10−5 mol) of 2$^A$,3$^A$-diamino-2$^A$,3$^A$-deoxy-β-cyclodextrin in 1 mL of water. The pH of the solution was adjusted to 10 with 1 M NaOH before a solution of 36.4 mg (8.80×10$^{-5}$ mol) of dithiobis(succinimidyl propionate) (DSP, Pierce Chemical Co. of Rockford, Ill.) in 1 mL of chloroform was added. The resulting biphasic mixture was agitated with a Vortex mixer for 0.5 h. The aqueous layer was then decanted and extracted with 3×1 mL of fresh chloroform. The aqueous polymer solution was then subjected to gel permeation chromatography.

Example 14

6$^A$,6$^D$-Bis-(2-aminoethylthio)-6$^A$6$^D$-deoxy-B-cyclodextrin, 14 (Tabushi, I: Shimokawa, K; Fugita, K. *Tetrahedron Lett.* 1977, 1527–1530)

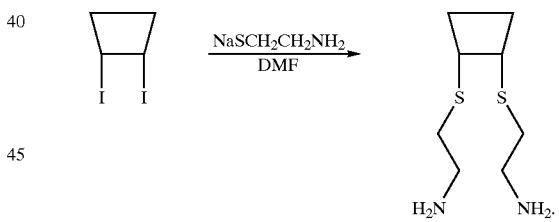

A 25 mL Schlenk flask equipped with a magnetic stirbar and a septum was charged with 0.91 mL (7.37 mmol) of a 0.81 M solution of sodium 2-aminoethylthiolate in ethanol. (Fieser, L. F.; Fiester, M. *Reagents for Organic Synthesis*; Wiley: New York, 1967; Vol. 3, pp. 265–266). The solution was evaporated to dryness and the solid was redissolved in 5 mL of anhydrous DMF (Aldrich). 6$^A$,6$^D$-Diiodo-6$^A$,6$^D$-deoxy-β-cyclodextrin (100 mg, 7.38×10$^{-5}$ mol was added and the resulting suspension was stirred at 60° C. under nitrogen for 2 h. After cooling to room temperature, the solution was concentrated in vacuo and the residue was redissolved in water. After acidifying with 0.1 N HCl, the solution was applied to a Toyopearl SP-650M ion-exchange column (NH$_4^+$ form) and the product was eluted with a 0 to 0.4 M ammonium bicarbonate gradient. Appropriate fractions were combined and lyophilized to dryness. This afforded 80 mg (79%) of 14 as a white powder.

Example 15

β-cyclodextrin(cystamine)-DTBP copolymer, 15

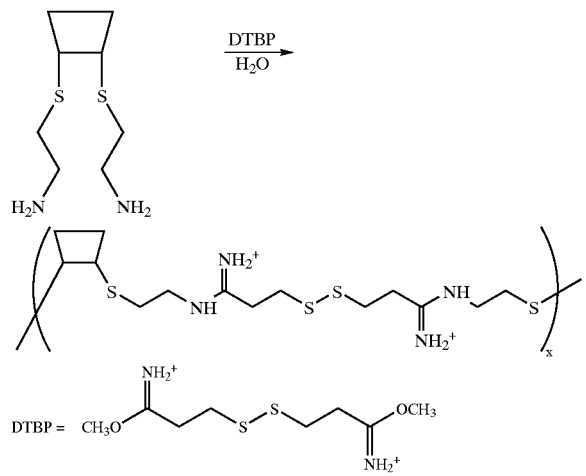

A 4 mL vial was charged with a solution of 19.6 mg ($1.42 \times 10^{-5}$ mol) of the bis(hydrogen carbonate) salt of 14 in 0.5 mL of 0.1 M $NaHCO_3$. The solution was cooled in an ice bath before 4.4 mg ($1.4 \times 10^{-5}$ mol) of dimethyl 3,3'-dithiobispropionimidate-2 HCl (DTBP, Pierce) was added. The resulting solution was then agitated with a Vortex mixer and allowed to stand at 0° C. for 1 h. The reaction was quenched with 1M Tris-HCl before it was acidified to pH 4 with 0.1 N HCl. The aqueous polymer solution was then subjected to gel permeation chromatography on Toyopearl HW-40F resin. Fractions were analyzed by GPC and appropriate fractions were lyophilized to dryness. This afforded 21.3 mg (100%) of 15 as a white powder.

Example 16

β-cyclodextrin(cystamine)-DMS copolymer, 16

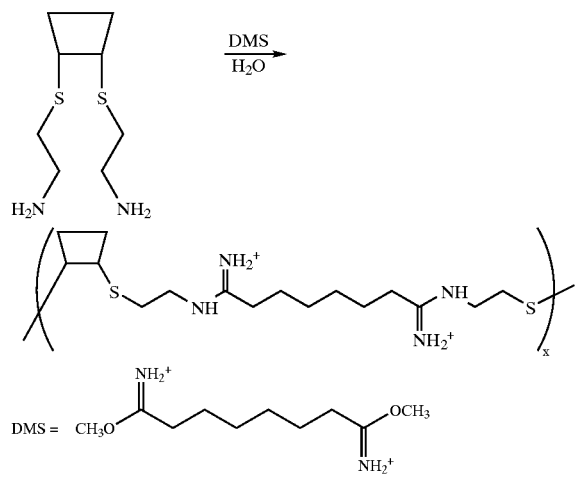

A 10 mL Schlenk flask equipped with a magnetic stirbar and a septum was charged with 200 mg ($1.60 \times 10^{-4}$ mol) of 14, 44 μL ($3.2 \times 10^{-4}$ mol) of triethylamine (Aldrich Chemical Co., Milwaukee, Wis.), 43.6 mg ($1.60 \times 10^{-4}$ mol) of dimethylsuberimidate.2HCl (DMS, Pierce), and 3 mL of anhydrous DMF (Aldrich Chemical Co., Milwaukee, Wis.). The resulting slurry was heated to 80° C. for 18 hours under a steady stream of nitrogen during which time most of the solvent had evaporated. The residue which remained was redissolved in 10 mL of water and the resulting solution was then acidified with 10% HCl to pH 4. This solution was then passed through an Amicon Centricon Plus-20 5,000 NMWL centrifugal filter. After washing with 2×10 mL portions of water, the polymer solution was lyophilized to dryness yielding 41.4 mg (18%) of an off-white amorphous solid.

Example 17

Folate Ligand Attachment to Cyclodextrin Polymer

1. Resin Coupling 50 mg of FMOC-$PEG_{3400}$-NHS (Shearwater Polymers, Inc. of Huntsville, Ala.) is dissolved in 1 mL of anhydrous N,N-dimethylformamide (DMF) and is added to 10 equivalents of hydrazide 2-chlorotrityl resin (Novabiochem USA of La Jolla, Calif.) swelled in DMF. The mixture is stirred at 60° C. until all the polymer is coupled to the resin, as determined by a GPC system equipped with a UV detector. The resin-polymer is then transferred to a sintered glass column for all further reactions.

2. Resin Capping

The unreacted hydrazide groups on the resins are capped with acetic anhydride and the acetic acid products are neutralized by diisopropylethylamine.

3. Removal of Protecting Group

The FMOC protecting group is removed by two washes with 20% piperidine in DMF (1 mL total volume). The resin is then washed 10 times with 1 mL DMF and 5 times with 1 mL $H_2O$.

4. Folic Acid Coupling 10 equivalents of folic acid and 1-(3-dimethylaminopropyl)-3-ethylcarbodiimide (EDC) is added to the resin along with 1.5 mL $H_2O$. 1N NaOH is added to the reaction mixture until the folic acid is dissolved (around pH 10). The glass column is then placed on a rotator and mixed overnight. The resin is then washed 10 times with 1 mL NaOH (1N), 10 times with 1 mL of 50 mM sodium bicarbonate, and then 5 times each with water, THF, and dichloromethane.

5. Cleavage from Resin

1% trifluoroacetic acid (TFA) in 1 mL DCM is added to the resin twice for 1 minute each. The supernatant is collected and DCM evaporated. The resulting oily film is rehydrated in $H_2O$ and lyophilized, resulting in a light yellow powder. An NMR is taken to confirm the presence of the PEG polymer.

6. Coupling to Polymer

Folic acid-linker is reacted with 6 equivalents of a cyclodextrin copolymer (oxidized as in Example 10) by mixing in 50 mmol borate (pH 8.5). The reaction mixture is analyzed and conjugation polymer confined by a GPC system with a UV detection at 285 nm.

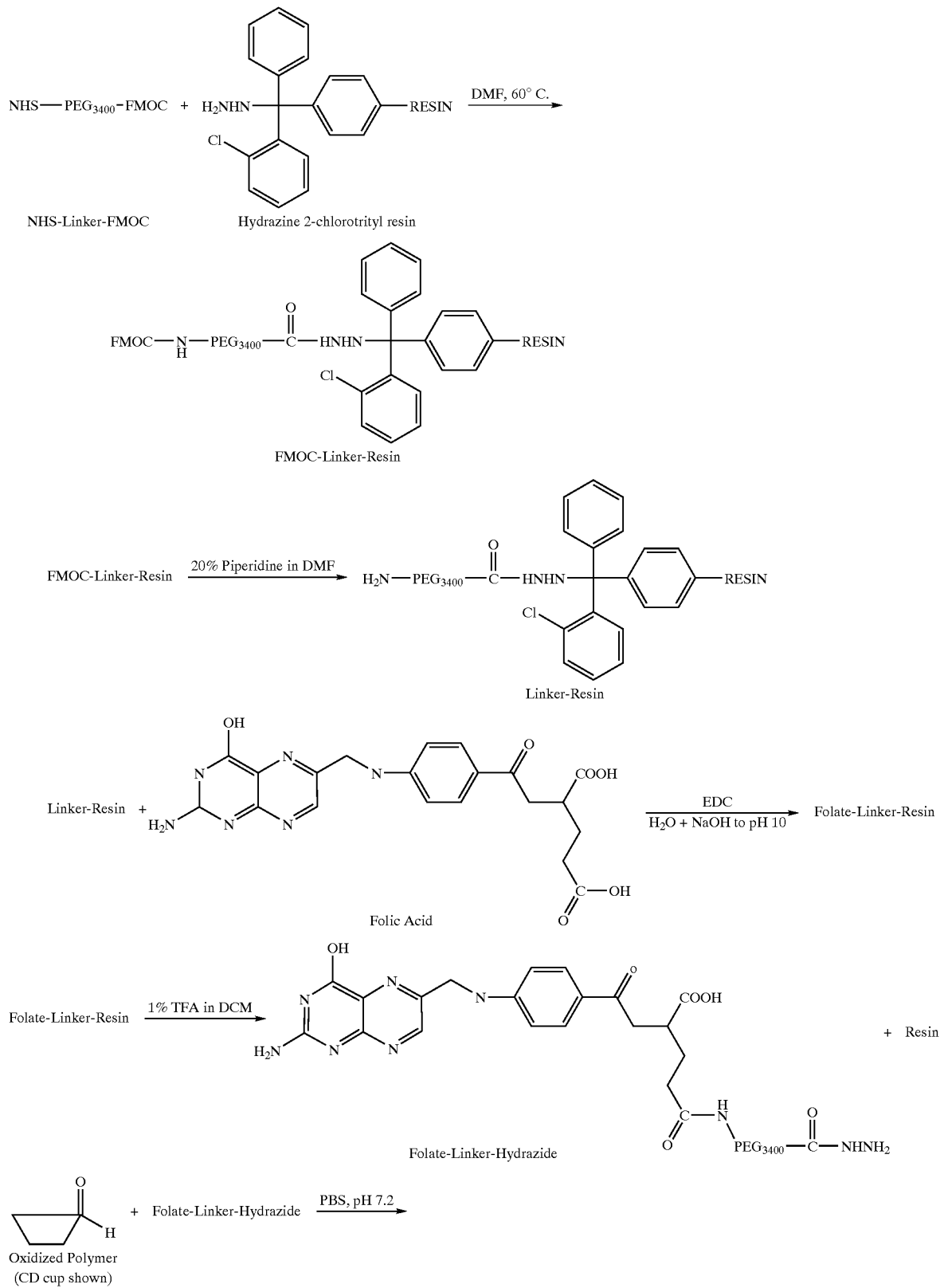

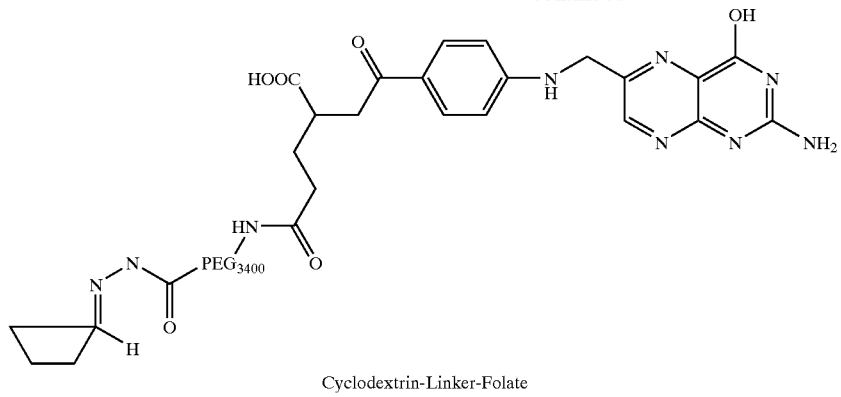

Cyclodextrin-Linker-Folate

Example 18

Folate Ligand Attachment to Cyclodextrin Polymer

1. Coupling 36 mg of t-butyl carbazate dissolved in 240 μL of DCM/ethyl acetate (1:1) was added to 260 mg of FMOC-PEG$_{3400}$-NHS (Shearwater Polymers) and mixed at room temperature for 2 hours. The product was precipitated two times from ethyl acetate/ether (1:1).

2. Removal of Protecting Group

FMOC protecting group was removed with 20% piperidine in DMF. The solvent was removed in vacuo and product redissolved in 1.3 mL of DMSO.

3. Folic Acid Coupling 1.2 equivalents of folic acid and DCC and one drop of pyridine was then added and the resulting solution stirred in the dark at room temperature for 6 hours. DMSO was removed in vacuo and conjugation of folic acid was confirmed by GPC with UV monitoring at 285 nm.

4. Removal of Hydrazide Protecting Group

Finally, the hydrazide was deprotected by stirring in 4M HCl in dioxane for 1 hour before removing the solvent in vacuo. The final product was purified by Toyopearl HW-40F column chromatography.

5. Coupling to Polymer

Folic acid-linker is reacted with 6 equivalents of a cyclodextrin copolymer (oxidized as in Example 10) by mixing in 50 mmol borate (pH 8.5). The reaction mixture is analyzed and conjugation polymer confirmed by a GPC system with a UV detection at 285 nm.

SYNTHESIS OF FOLIC ACID-PEG-HYDRAZINE

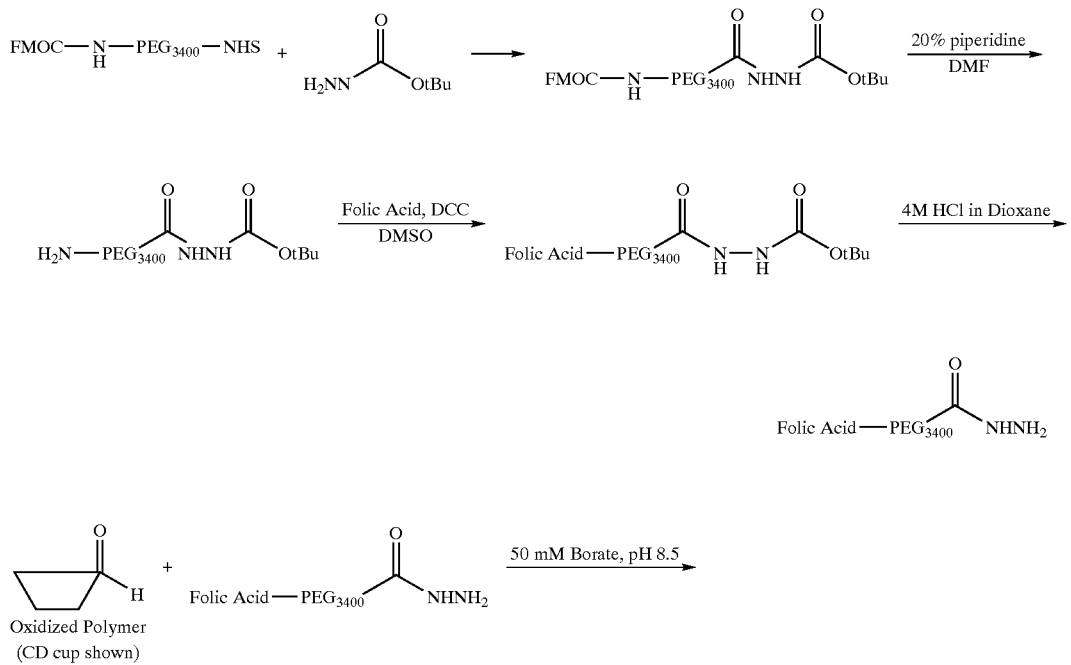

-continued

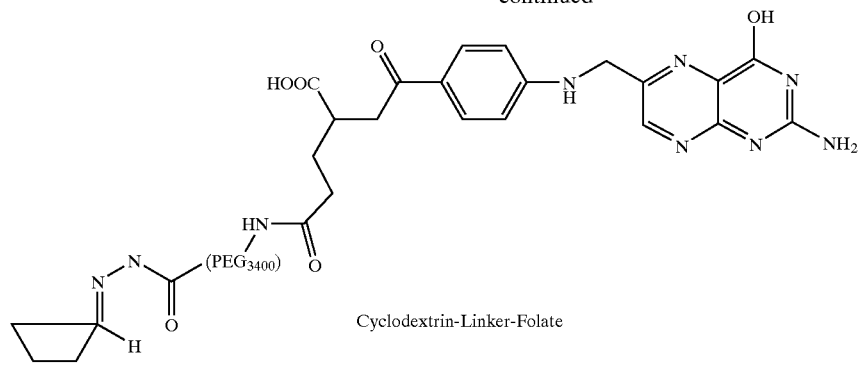

Cyclodextrin-Linker-Folate

Example 19

Transferrin Ligand Attachment to Cyclodextrin Polymer

1. Transferrin Oxidation 500 mg of iron-free human transferrin (Sigma of St. Louis, Mo.) is dissolved in 30 mM sodium acetate buffer and cooled to 0° C. To this solution is added 20 mg of sodium periodate dissolved in 4 μL of 30 mM sodium acetate. The mixture is stirred at 0° C. overnight. Next 1 g of AG501-X8 resin (Biorad) is added to remove salts before the solution is lyophilized.

2. Resin Coupling 20 mg of FMOC-PEG$_{3400}$-NHS (Shearwater Polymers, Inc. of Huntsville, Ala.) was dissolved in 0.5 mL of anhydrous N,N-dimethylformamide (DMF) and added to 10 equivalents of hydrazide 2-chlorotrityl resin (Novabiochem USA of La Jolla, Calif.) swelled in DMF. The mixture was stirred at 60° C. until all the polymer was coupled to the resin, as determined by a GPC system equipped with an ultraviolet (UV) detector. The resin-polymer was then transferred to a sintered glass column for all further reactions.

3. Resin Capping

The unreacted hydrazide groups on the resins were capped with acetic anhydride and the acetic acid products were neutralized by diisopropylethylamine.

4. Removal of Protecting Group

The FMOC protecting group was removed by two washes with 20% piperidine in DMF (1 mL total volume). The resin was then washed 10 times with 1 mL DMF and 5 times with 1 mL H$_2$O.

5. Transferrin Coupling

To the resin is added 1.2 equivalents of transferrin dissolved in 0.05 M sodium carbonate and 0.1 M sodium citrate buffer, pH 9.5. 5 M cyanoborahydride in 1N NaOH is then added to the solution. The glass column is placed on a rotator and mixed for 2 hours. The resin is then washed 15 times with water and 5 times each with tetrahydrofuran (THF) and DCM.

6. Cleavage from Resin

1% trifluoroacetic acid (TFA) in 1 mL DCM is added to the resin twice for 1 minute each. The supernatant is then collected and DCM evaporated. The resulting oily film is rehydrated in H$_2$O and lyophilized.

7. Coupling to Polymer

Transferrin linker is reacted with 6 equivalents of a cyclodextrin copolymer by reductive animation with sodium cyanoborohydride: first, the copolymer is added to transferrin linker dissolved in 0.05 M sodium carbonate and 0.1 M sodium citrate buffer. 5 M cyanoborohydride in 1N NaOH is added and the reaction is stirred for 2 hours at room temperature. Unreacted aldehyde sites are blocked by adding ethanolamine and reacting for 15 minuted at room temperature. The resulting conjugate is purified by dialysis.

TRANSFERRIN ATTACHMENT TO CYCLODEXTRIN POLYMER

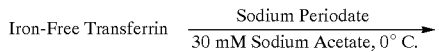

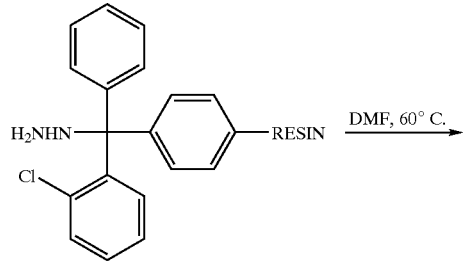

Hydrazine 2-chlorotrityl resin

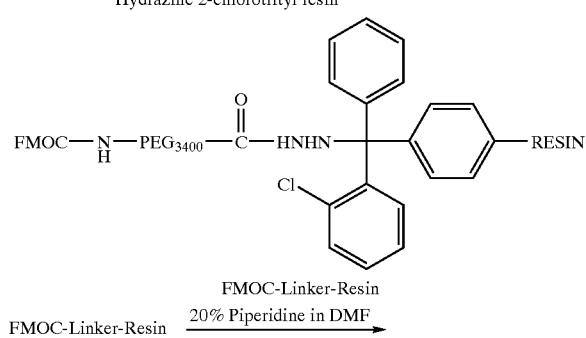

FMOC-Linker-Resin

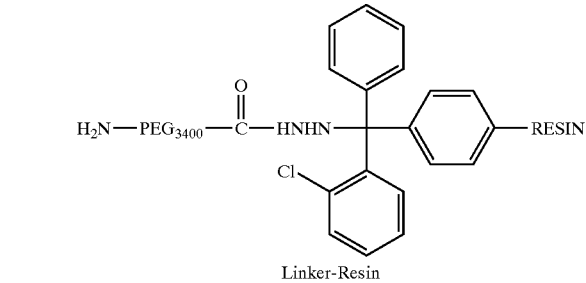

Linker-Resin

TRANSFERRIN ATTACHMENT TO CYCLODEXTRIN POLYMER

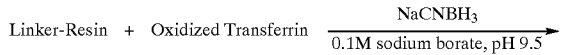

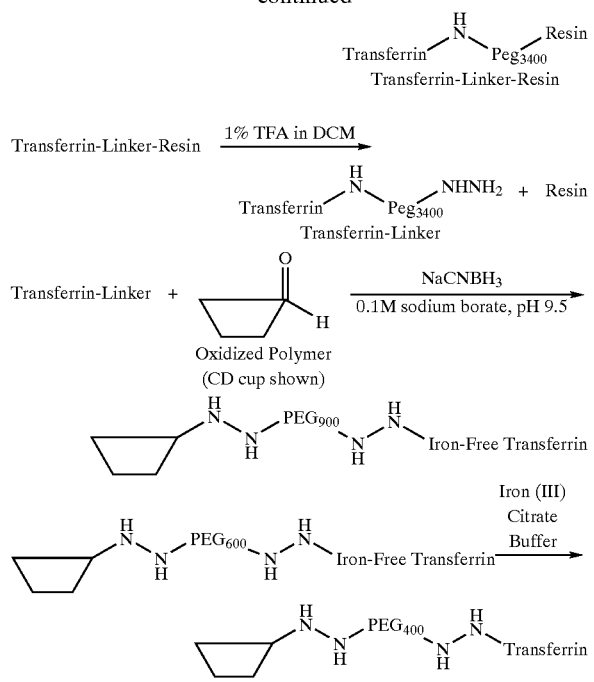

Example 20

General Procedure for Cyclodextrin Copolymer Complexation with Small Molecules

Cyclodextrin-based copolymer (CD-polymer) is dissolved in water, buffer, or organic solvent at the appropriate concentration. The small molecule is dissolved in a solvent miscible with the solvent of the CD-polymer solution and is added to the CD-polymer solution. The mixture is then stirred for ½ hour and then allowed to come to equilibrium overnight.

Example 21

Cyclodextrin Copolymer Complexation with Doxorubicin

Doxorubicin and CD-polymer were dissolved at various concentrations in PBS (phosphate buffered saline, pH 7.2). The association constant between the CD and doxorubicin was determined by measuring the extent of doxorubicin's fluorescence increase upon complexation with the CD. (The hydrophobic interaction between the CD and doxorubicin enhances the fluorescence intensity). Association constant was approximately 200 $M^{-1}$ at pH 7.1. Addition of β-CD consistently enhanced doxorubicin fluorescence, indicating complexation between the CD-polymer and doxorubicin. Husain et al., *Applied Spectroscopy* Vol. 46, No. 4, 652–658 (1992) found the association constant between β-CD and doxorubicin to be 210 $M^{-1}$ at pH 7.1.

Example 22

Small Molecule Delivery to Cultured Cells

Media containing doxorubicin and doxorubicin/CD-polymer complexes at various concentrations were applied to cultured cell lines. After 5 hours, the media was removed and replaced with fresh media. Doxorubicin effect on cell survival was determined by the MTT ([3-(4,5-dimethylthiazol-2-yl)-2,5-diphenyl-2H-tetrazolium) toxicity assay. (R. Ian Feshney, "*Culture of Animal Cells*", 3rd ed., Wiley-Liss:New York (1994)). The results are illustrated in the table below. Copolymer 15 or 16 (138 μM equivalent of CD monomer) was not toxic to KB or KB-VI (a multidrug resistant derivative of KB) cell lines in the absence of doxorubicin. For receptor-mediated delivery, a ligand such a folate is covalently attached to the CD-polymer used for doxorubicin complexation.

| Cell Line | CD-polymer | $IC_{50}$ (μM of doxorubicin) |
|---|---|---|
| KB | none | ~0.1 |
| KB-VI (multidrug resistant) | none | ~10 |
| KB-VI | copolymer 15 or 16 (138 μM equivalent of CD monomer) | ~2–3 |

Example 23

Fixed Permanent Charged Copolymer Complexation with Plasmid

In general, equal volumes of fixed charged CD-polymer and DNA plasmid solutions in water are mixed at appropriate polymer/plasmid charge ratios. The mixture is then allowed to equilibrate and self-assemble at room temperature overnight. Complexation success is monitored by transferring a small aliquot of the mixture to 0.6% agarose gel and checking for DNA mobility. Free DNA travels under an applied voltage, whereas complexed DNA is retarded at the well.

1 μg of DNA at a concentration of 0.2 μg/μL in distilled water was mixed with 10 μL of copolymer 15 at polymer amine: DNA phosphate charge ratios of 2, 4, 6, 12, 24, 36, 60, and 120. The solution was mixed manually by a micropipette and then gently mixed overnight on a lab rotator. 1 μg/μL of loading buffer (40% sucrose, 0.25% bromophenol blue, and 200 mM Tris-Acetate buffer containing 5 mM EDTA (Gao et al., *Biochemistry* 35:1027–1036 (1996)) was added to each solution the following morning. Each DNA/polymer sample was loaded on a 0.6% agarose electrophoresis gel containing 6 μg of EtBr/100 mL in 1×TAE buffer (40 mM Tris-acetate/1 mM EDTA) and 40V was applied to the gel for 1 hour. The extent of DNA/polymer complexation was indicated by DNA retardation in the gel migration pattern. The polymer (15) retarded DNA at charge ratios of 6 and above, indicating complexation under these conditions.

Example 24

Crosslinking Copolymer Complexation with Plasmid

Copolymer 15 or copolymer 16 is oxidized as in Example 10. Oxidized copolymer 15 or 16 is then complexed with a DNA plasmid as in Examples 23 and 26. A crosslinking agent (for example, $PEG_{600}$-Dihydrazide) is then added to encapsulate the DNA. Encapsulation success is determined by light scattering and visualized by electron microscopy.

Example 25

Variably Charged (pH-sensitive) Copolymer Complexation with Plasmid

Equal volumes of a CD-polymer and DNA plasmid solutions in water are mixed in appropriate polymer/plasmid charge ratios. The pH of the mixture is adjusted to form a charged CD-polymer. The mixture is then allowed to equilibrate and self-assemble at room temperature for 30 minutes.

A crosslinking agent (for example, PEG$_{600}$-Dihydrazide) is then added to encapsulate the DNA. A concentrated buffer solution is then added to render the pH and thus the CD-polymer neutral. Encapsulation success is determined by light scattering and visualized by electron microscopy.

Example 26

Transfection Studies with Plasmids Encoding Luciferase Reporter Gene

Figure 1B:
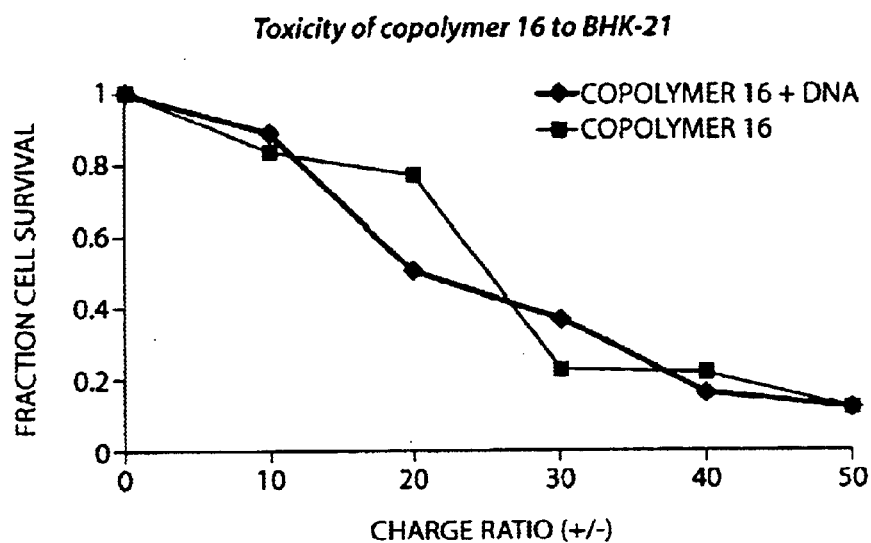
FIG. 1B shows transfection studies with plasmids encoding *Luciferase* reporter gene particularly noting the toxicity of copolymer 16 to BHK-21.

BHK-21 cells were plated in 24 well plates at a cell density of 60,000 cells/well 24 hours before transfection. Plasmids encoding the luciferase gene were encapsulated by the CD-polymer as in Examples 23 or 25 such that the DNA/polymer complexes were assembled at polymer amine: DNA phosphate charge ratios of 6, 12, 24, 36, and 60 as described in DNA binding studies of Example 23. Media solution containing the DNA/polymer complexes was added to cultured cells and replaced with fresh media after 5 hours of incubation at 37° C. The cells were lysed 48 hours after transfection. Appropriate substrates for the luciferase light assay were added to the cell lysate. Luciferase activity, measured in terms of light units produced, was quantified by a luminometer. The results are shown in FIG. 1A. DNA/polymer complexes successfully transfected BHK-21 cells at a charge ratios of 6, 12, and 24. Cell lysate was also used to determine cell viability by the Lowry protein assay. (Lowry et al., Journal of Biological Chemistry, Vol. 193, 265–275 (1951)). The results are shown in FIG. 1B. Maximum toxicity was seen at a polymer amine: DNA phosphate charge ratios of 36 and 60 with 91% cell survival.

Example 27

Transfection Studies with Plasmids Encoding Luciferase Reporter Gene

BHK-21 cells were plated in 24 well plates at a cell density of 60,000 cells/well 24 hours before transfection. Plasmids encoding the luciferase gene were encapsulated by the CD-polymer as in Example 23 except copolymer 15 was replaced with copolymer 16 and that the DNA/polymer complexes successfully transfected BHK-21 cells at charge ratios of 10, 20, 30, and 40 with maximum transfection at polymer amine:DNA phosphate charge ratio of 20. Media solution containing the DNA/polymer complexes was added to cultured cells and replaced with fresh media after 24 hours of incubation at 37° C. The cells were lysed 48 hours after transfection. Appropriate substrates for the luciferase light assay were added to the cell lysate. Luciferase activity, measured in terms of light units produced, was quantified by a luminometer. The results are shown in FIG. 1A. DNA/polymer complexes successfully transfected BHK-21 cells at a charge ratios of 6, 12, and 24. Cell lysate was also used to determine cell viability by the Lowry protein assay. (Lowry et al., Journal of Biological Chemistry, Vol. 193, 265–275 (1951)). The results are shown in FIG. 1B. Maximum toxicity was seen at a polymer amine: DNA phosphate charge ratios of 40 and 50 with 33% cell survival.

Example 28

Transfection Studies with Plasmids Encoding GFP Reporter Gene

Plasmids encoding the green fluorescent protein are encapsulated by the CD-polymer as in Examples 23 or 25. Media solution containing the DNA/polymer complexes is added to cultured cells and replaced with fresh media after 5 hours of incubation at 37° C. The cells are detached from the surface with trypsin, washed, and resuspended in Hanks Balanced Salt Solution with propidium iodide. The cells are then analyzed by fluorescence activated cell sorting (FACS). Cell viability is determined by cell size and propidium iodide exclusion, and transfection success by GFP protein fluorescence.

Example 29

Polymer Complexation with Oligos

Complexation with antisense oligos is accomplished following the procedures for plasmid complexation of Examples 23 or 25.

Example 30

Transfection Studies with Oligos

Antisense oligos directed against the luciferase gene are encapsulated by the CD-polymer as described in Example 29. Media solution containing the oligo/polymer complexes is added to HeLa X1/5 cells (HeLa cells that constitutively express the luciferase gene, donated by CLONTECH) and replaced with fresh media after 5 hours of incubation at 37° C. Cells are lysed 48 hours after transfection and appropriate substrates for the luciferase assay are added to the lysates. Luciferase activity, measured in terms of light units produced, is quantified by a luminometer. Transfection success is determined by knockout of luciferase activity.

Example 31

Toxicity of β-cyclodextrin(cystamine)-DTBP copolymer, 15

The acute toxicity of copolymer 15 was investigated using Swiss-Webster "white mice." A total of 48 mice were used as described in the table below. Single intravenous (i.v.) or intraperitoneal (i.p.) injections of sterile saline solutions or of copolymer 15 were given to the mice. The animals were followed for five days after which they sacrificed and gross necropsy performed. No mortality and no toxicity was observed.

| Group No. | #/Sex (M/F) | Copolymer | Concentration (mg/mL) | Dose Volume (mL) | Dose (mg) | Treatment Regimen |
| --- | --- | --- | --- | --- | --- | --- |
| 1 | 3/3 | CoPolymer 15 | 0.5275 | 0.1 | 0.05 | i.v., once |
| 2 | 3/3 | CoPolymer 15 | 5.275 | 0.1 | 0.53 | i.v., once |
| 3 | 3/3 | CoPolymer 15 | 52.75 | 0.1 | 5.28 | i.v., once |
| 4 | 3/3 | CoPolymer 15 | 0.5275 | 0.1 | 0.05 | i.p., once |
| 5 | 3/3 | CoPolymer 15 | 5.275 | 0.1 | 0.53 | i.p., once |
| 6 | 3/3 | CoPolymer 15 | 52.75 | 0.1 | 5.28 | i.p., once |
| 7 | 3/3 | 0.9% saline | 0.000 | 0.1 | 0.00 | i.v., once |
| 8 | 3/3 | 0.9% saline | 0.000 | 0.1 | 0.00 | i.p., once |

Example 32

Transfection Studies with Plasmids Encoding Luciferase Reporter Gene

Figure 2A:
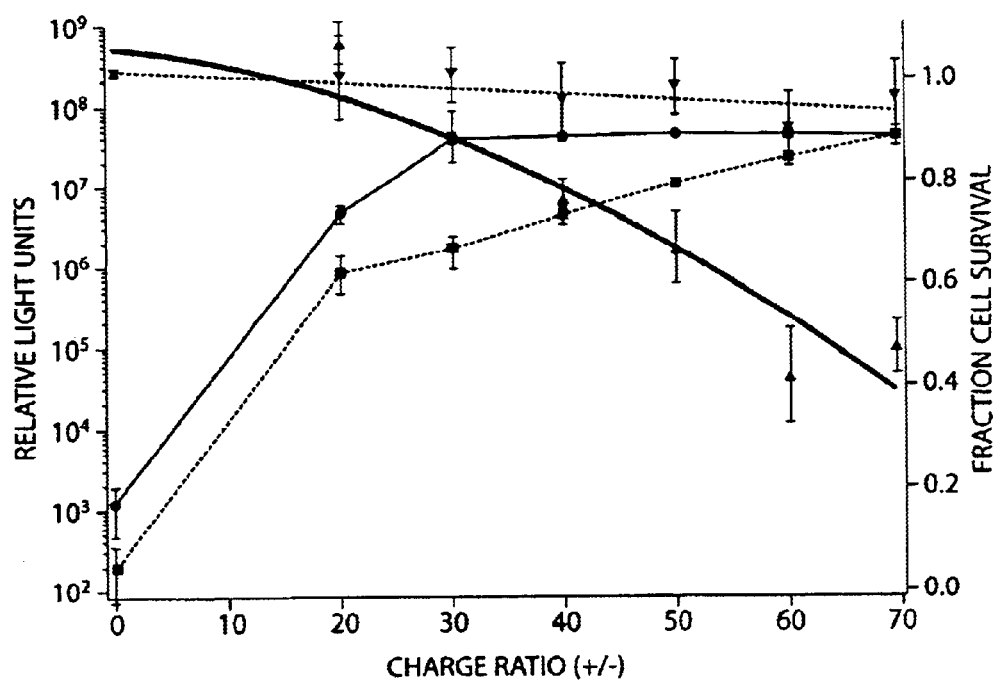
FIG. 2A shows the effect of copolymer 16/DNA charge ratio and serum conditions on transfection efficiency (● and ■) and cell survival (▼ and ▲) in BHK-21 cells. Result from transfection in 10% serum and serum-free media are shown as, respectively, dotted and solid lines. Data are reported at the mean +/− S.D. of three samples. Toxicity data are presented as best fit lines.
Figure 2B:
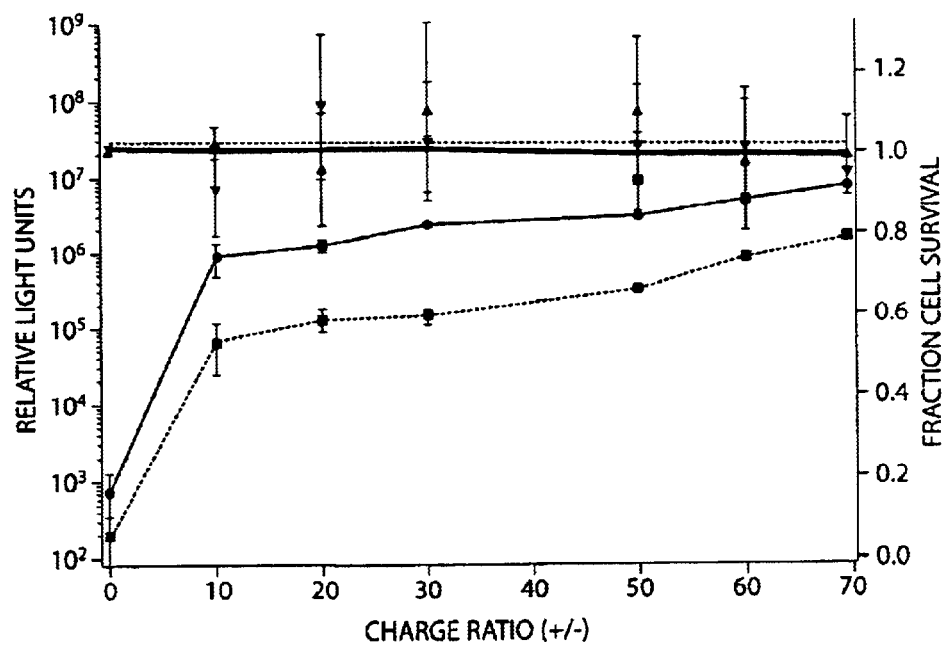
FIG. 2B shows the effect of copolymer 16/DNA charge ratio and serum conditions on transfection efficiency (● and ■) and cell survival (▼ and ▲) in CHO-K1 cells. Results from transfection in 10% serum and serum-free media are shown as, respectively, dotted and solid lines. Data are reported at the mean +/– S.D. of three samples. Toxicity data are presented as best fit lines.

Plasmids encoding the luciferase gene were encapsulated by the CD-polymer as in Example 23 except copolymer 15 was replaced with copolymer 16. The DNA/polymer complexes were use to successfully transfect BHK-21 or CHO-K1 cells, each plated in 24 well plates at a cell density of 60,000 cells/well 24 hours before transfection, at various charge ratios in 10% serum and serum-free conditions following the procedure outlined in Example 27. The cells were lysed 48 hours after transfection. Appropriate substrates for the luciferase light assay were added to the cell lysate. Luciferase activity, measured in terms of light units produced (i.e., relative light units (RLU)), was quantified by a luminometer. Cell lysate was also used to determine cell viability by the Lowry protein assay. (Lowry et al., *Journal of Biological Chemistry*, Vol. 193, 265–275 (1951)). Toxicity was measured by determining total cellular protein in the wells 48 hours after transfection. The transfection and cell survival results in 10% serum and serum free media are shown in FIGS. 2A and 2B.

Luciferase protein activity in BHK-21 cells transfected in serum-free conditions reached a stable maximum at 30+/− with ~$5 \times 10^7$ RLUs. The presence of 10% serum in the transfection media decreased luciferase activity at all charge ratios except 70+/−. With CHO-K1 cells, increasing charge ratio also enhanced the transfection for all conditions tested. Additionally, transfection in serum decreased light units by an order of magnitude.

Copolymer 16 showed toxicity only to BHK-21 cells for transfections in the absence of serum. Toxicity was minimized with the presence of 10% serum during transfection. No noticeable toxicity was observed from transfections to CHO-K1 cells.

Figure 3A:
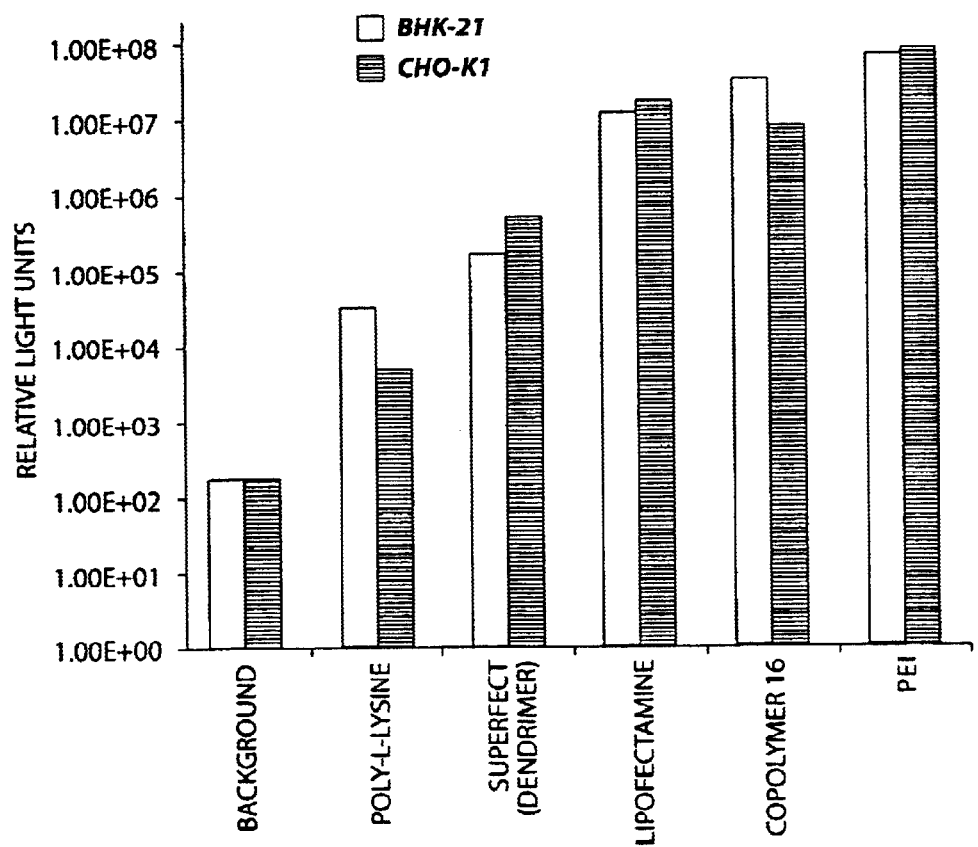
FIG. 3A shows transfection studies with plasmids encoding *Luciferase* reporter gene particularly noting the relative light units.
Figure 3B:
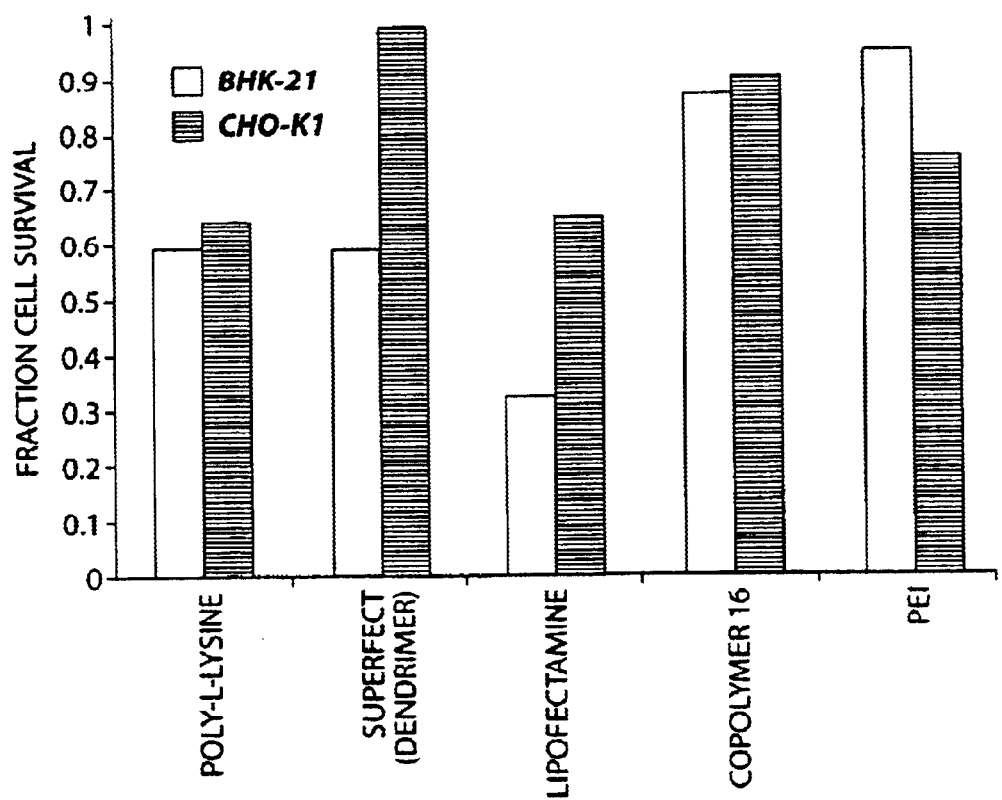
FIG. 3B shows transfection studies with plasmids encoding *Luciferase* reporter gene particularly noting the fraction cell survival.

Following the procedure of Example 32, transfection efficiency and toxicity of various non-viral vectors with BHK-21 and CHO-K1 cells were studied and compared against those achieved with DNA/copolymer 16 complexes. The BHK-21 and CHO-K1 cells were transfected at a range of charge ratios and starting cells densities for all vectors in serum-free media. The results are shown in FIGS. 3A and 3B and illustrate the optimum transfection conditions found for each vector.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The claimed invention is:

1. A water-soluble, linear cyclodextrin copolymer comprising repeating units of formula VIa, VIb, or both:

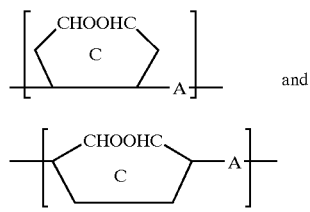

wherein C is a substituted or unsubstituted oxidized cyclodextrin monomer and A is a comonomer bound to cyclodextrin C.

2. A cyclodextrin copolymer of claim 1, wherein said cyclodextrin monomer is an α-, β-, γ-cyclodextrin, or combination thereof.

3. The copolymer of claim 1, wherein A is selected from:
—HNC(O)(CH$_2$)$_x$C(O)NH—, —HNC(O)(CH$_2$)$_x$SS(CH$_2$)$_x$C(O)NH—, —$^+$H$_2$N(CH$_2$)$_x$SS(CH$_2$)$_x$NH$_2$$^+$—,
—HNC(O)(CH$_2$CH$_2$O)$_x$CH$_2$CH$_2$C(O)NH—,
—HNNHC(O)(CH$_2$CH$_2$O)$_x$CH$_2$CH$_2$C(O)NHNH—,
—$^+$H$_2$NCH$_2$(CH$_2$CH$_2$O)$_x$CH$_2$CH$_2$CH$_2$NH$_2$$^+$—,
—HNC(O)(CH$_2$CH$_2$O)$_x$CH$_2$CH$_2$SS(CH$_2$CH$_2$O)$_x$CH$_2$CH$_2$C(O)NH—, —HNC(NH$_2$$^+$)(CH$_2$CH$_2$O)$_x$CH$_2$CH$_2$C(NH$_2$$^+$)NH—, —SCH$_2$CH$_2$NHC(NH$_2$$^+$)(CH$_2$)$_x$C(NH$_2$$^+$)NHCH$_2$CH$_2$S—, —SCH$_2$CH$_2$NHC(NH$_2$$^+$)(CH$_2$)$_x$SS(CH$_2$)$_x$C(NH$_2$$^+$)NHCH$_2$CH$_2$S—, —SCH$_2$CH$_2$NHC(NH$_2$$^+$)CH$_2$CH$_2$(OCH$_2$CH$_2$)$_x$C(NH$_2$$^+$)NHCH$_2$CH$_2$S—,

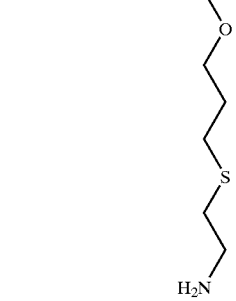

—HNC(O)(CH$_2$CH$_2$O)$_y$(CHCH$_2$O)$_z$CH$_2$CH$_2$C(O)NH—,

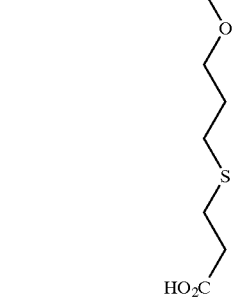

—HNC(O)(CH$_2$CH$_2$O)$_y$(CHCH$_2$O)$_z$CH$_2$CH$_2$C(O)NH—,

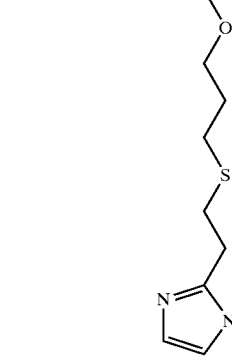

—HNC(O)(CH$_2$CH$_2$O)$_y$(CHCH$_2$O)$_z$CH$_2$CH$_2$C(O)NH—,

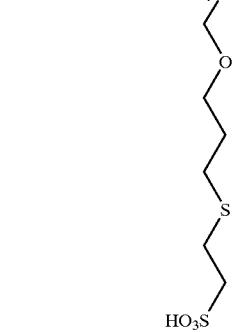

-continued

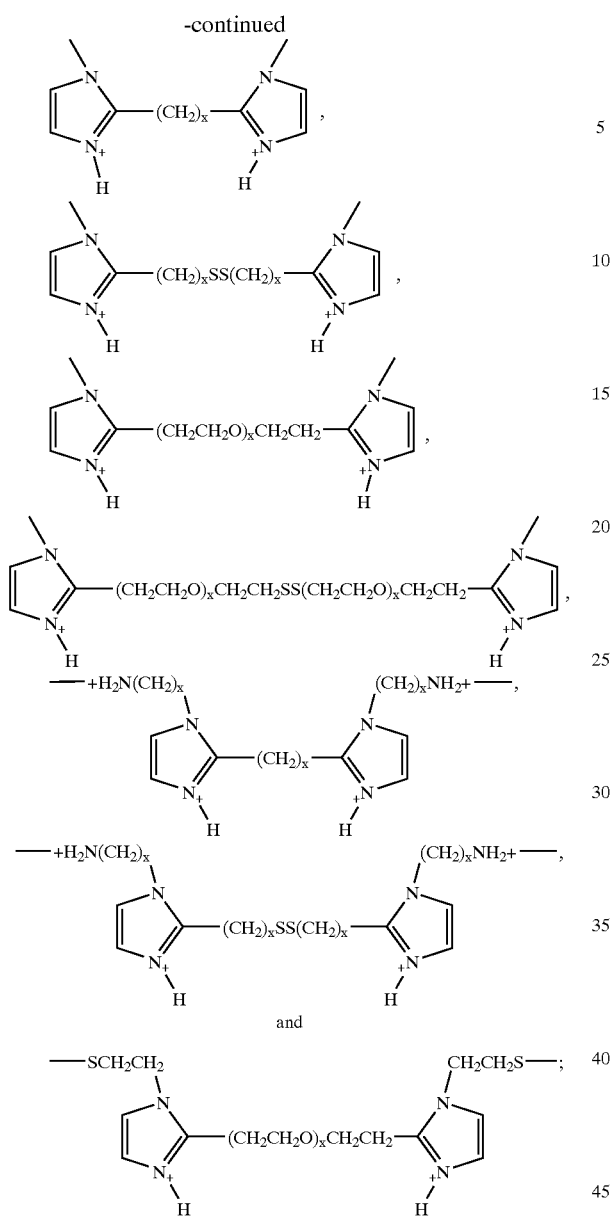

where x=1–50 and y+z=x.

4. The copolymer of claim 1, wherein A is biodegradable or acid-labile.

5. The copolymer of claim 1, wherein the cyclodextrin copolymer is crosslinked to a polymer.

6. The copolymer of claim 5, further comprising wherein at least one ligand is bound to the linear cyclodextrin copolymer; wherein said ligand allows the copolymer to target and bind to a cell.

7. The copolymer of claim 1, further comprising wherein at least one ligand is bound to the linear cyclodextrin copolymer; wherein said ligand allows the copolymer to target and bind to a cell.

8. The copolymer of claim 1, wherein substantially all of the repeating units are of formula VIa, VIb, or both.

9. The copolymer of claim 1, wherein all of the repeating units are of formula VIa, VIb, or both.

10. A therapeutic composition comprising the copolymer of claim 1, 5, 6, or 7 and a therapeutic agent.

11. A method of preparing a water-soluble linear oxidized cyclodextrin copolymer, comprising:

oxidizing a water-soluble, linear cyclodextrin copolymer having repeating units of formula Ia, Ib, or a combination thereof:

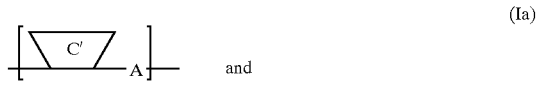
(Ia)

(Ib)

wherein C' is a substituted or unsubstituted cyclodextrin monomer and A is a comonomer bound to cyclodextrin monomer C'.

12. The method of claim 11, further comprising reacting said water-soluble, linear oxidized cyclodextrin copolymer with a ligand to form a water-soluble, linear oxidized cyclodextrin copolymer having at least one ligand bound to the copolymer, wherein said ligand allows the copolymer to target and bind to a cell.

13. A method of preparing a water-soluble, linear oxidized cyclodextrin copolymer, comprising:

(a) iodinating an oxidized cyclodextrin monomer precursor to form an oxidized diiodinated cyclodextrin monomer precursor formula VIIa, VIIb, VIIc or a mixture thereof:

VIIa

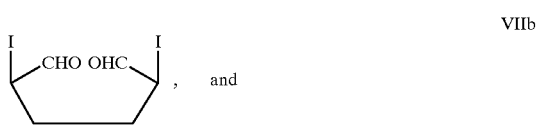
VIIb

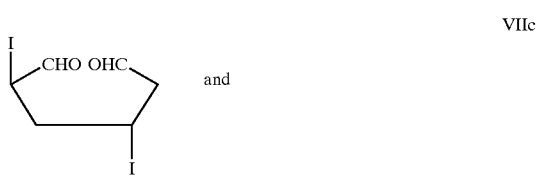
VIIc (b) copolymerizing said oxidized diiodinated cyclodextrin monomer precursor with a comonomer A precursor to form a linear oxidized cyclodextrin copolymer having a repeating units of formula VIa, VIb, or a combination thereof:

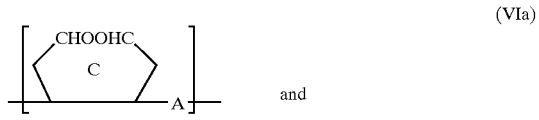
(VIa)

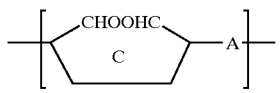
(VIb)

wherein C is a substituted or unsubstituted oxidized cyclodextrin monomer and A is a comonomer bound to the cyclodextrin comonomer C.

14. The method of claim 13, further comprising reacting said water-soluble, linear oxidized cyclodextrin copolymer with a ligand to form a water-soluble, linear oxidized cyclodextrin copolymer having at least one ligand bound to the copolymer, wherein said ligand allows the copolymer to target and bind to a cell.

15. The method of claim 13, further comprising aminating said oxidized diiodinated cyclodextrin monomer precursor to form an oxidized diaminated cyclodextrin monomer precursor of formula VIIIa, VIIIb, VIIIc or a mixture thereof:

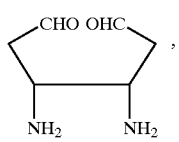
VIIIa

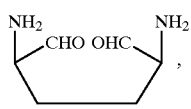
VIIIb, and

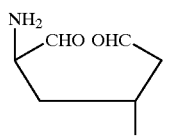
VIIIc, and

copolymerizing said oxidized diaminated cyclodextrin monomer precursor with a comonomer A precursor to form said water-soluble linear oxidized cyclodextrin copolymer having repeating units of formula VIa, VIb, or a combination thereof.

16. The method of claim 13, further comprising aminating said oxidized diiodinated cyclodextrin monomer precursor to form an oxidized diaminated cyclodextrin monomer precursor of formula IXa, IXb, IXc, or a mixture thereof:

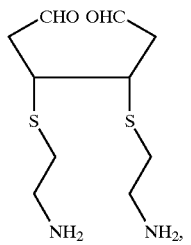
VIIIa

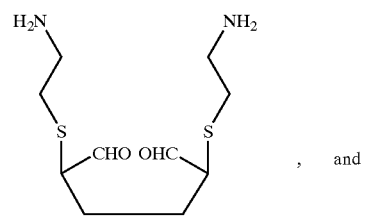
VIIIb, and

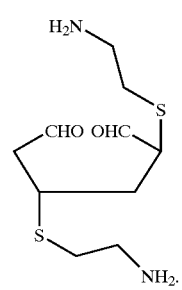
VIIIc

17. A method of producing a crosslinked cyclodextrin polymer comprising:

reacting at least one water-soluble, linear cyclodextrin copolymer having repeating units of formula VIa, VIb or a combination thereof:

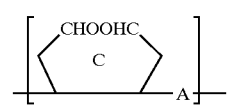
(VIa)

and

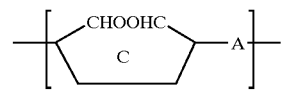
(VIb)

where C is a substituted or unsubstituted oxidized cyclodextrin monomer and A is a comonomer bound to cyclodextrin monomer C, with a polymer in the presence of a crosslinking agent.

18. The method of claim 17, wherein said polymer is a water-soluble, linear oxidized cyclodextrin copolymer.

19. A method of delivering a therapeutic agent comprising administering a therapeutically effective amount of the therapeutic composition of claim 10.

* * * * *